(12) United States Patent
Osborn, III

(10) Patent No.: US 6,231,556 B1
(45) Date of Patent: *May 15, 2001

(54) GENERALLY THIN, FLEXIBLE SANITARY NAPKIN WITH STIFFENED CENTER

(75) Inventor: Thomas Ward Osborn, III, Cincinnati, OH (US)

(73) Assignee: The Procter & Gamble Company, Cincinnati, OH (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/665,595

(22) Filed: Jun. 18, 1996

Related U.S. Application Data

(63) Continuation of application No. 08/530,456, filed on Sep. 19, 1995, now abandoned, which is a continuation of application No. 08/161,215, filed on Dec. 2, 1993, now abandoned, which is a continuation of application No. 07/874,872, filed on Apr. 28, 1992, now abandoned, which is a continuation-in-part of application No. 07/605,583, filed on Oct. 29, 1990, now abandoned, and a continuation-in-part of application No. 07/734,392, filed on Jul. 23, 1991, now abandoned, and a continuation-in-part of application No. 07/734,404, filed on Jul. 23, 1991, now abandoned, and a continuation-in-part of application No. 07/734,405, filed on Jul. 23, 1991, now Pat. No. 5,334,176, and a continuation-in-part of application No. 07/810,774, filed on Dec. 17, 1991, now abandoned.

(51) Int. Cl.$^7$ .................................................. A61F 13/15
(52) U.S. Cl. ............. 604/385.1; 604/387; 604/385.101; 604/358
(58) Field of Search .................................. 604/358, 378, 604/379, 380, 382, 385.1, 387, 385.101

(56) References Cited

U.S. PATENT DOCUMENTS

| 810,121 | * | 1/1906 | Green ................................... 604/378 |
| 810,123 | * | 1/1906 | Green ................................... 604/378 |
| 810,128 | * | 1/1906 | Green ................................... 604/378 |
| 4,195,634 | * | 4/1980 | DiSalvo et al. ..................... 604/359 |
| 5,248,309 | | 9/1993 | Serbiak et al. . |
| 5,466,232 | * | 11/1995 | Cardieux et al. .................... 604/378 |

FOREIGN PATENT DOCUMENTS

0316771 * 5/1989 (EP) ..................................... 604/358

* cited by examiner

*Primary Examiner*—Glenn K. Dawson
*Assistant Examiner*—Michele Kidwell
(74) *Attorney, Agent, or Firm*—Jeffrey V. Bamber

(57) ABSTRACT

A generally thin, flexible sanitary napkin capable of absorbing medium to high menstrual flows, and having a stiffened center is provided. In one embodiment, the sanitary napkin has a longitudinal central region is disposed along the length of at least a portion of the longitudinal centerline, and longitudinal side regions are disposed outboard of the longitudinal central region. The longitudinal central region of the sanitary napkin has a flexure-resistance that is greater than that of the longitudinal side regions. The embodiment of the sanitary napkin described above easily forms around the curvature of the wearer's labia majora by cupping and surrounding the exterior of the labia majora. The longitudinal central region of the sanitary napkin forms the bottom of a cup-like trough under the wearer's labia majora, and the longitudinal side regions are sufficiently flexible that they are able to form the sides of the trough structure.

19 Claims, 15 Drawing Sheets

GENERALLY THIN, FLEXIBLE SANITARY NAPKIN WITH STIFFENED CENTER

This is a continuation of application Ser. No. 08/530,456, filed on Sept. 19, 1995, now abandoned which was a continuation of application Ser. No. 08/161,215, filed on Dec. 2, 1993, (now abandoned) which was a continuation of application Ser. No. 07/874,872 filed on Apr. 28, 1992 (now abandoned), which was a continuation-in-part of the following U.S. patent applications: Ser. No. 07/605,583, filed on Oct. 29, 1990 abandoned; Ser. Nos. 07/734,392 abandoned, 07/734,404 abandoned, and 07/734,405 U.S. Pat. No. 5,334,176, filed on Jul. 23, 1991; and Ser. No.07/810,774, filed Dec. 17, 1991 abandoned.

FIELD OF THE INVENTION

The present invention relates to absorbent articles, such as sanitary napkins. More particularly, the present invention relates to a generally thin, flexible sanitary napkin that is provided with a stiffened center.

BACKGROUND OF THE INVENTION

This invention is concerned with absorbent articles such as sanitary napkins, pantiliners, and incontinent pads that are designed to absorb and retain liquid and other discharges from the human body and to prevent body and clothing soiling. The present invention is particularly concerned with sanitary napkins that are generally relatively thin and flexible.

Sanitary napkins of a wide variety of shapes and dimensions are currently used by women for the collection of menses and other bodily discharges.

With respect to sanitary napkins, at least two general classes pertinent to the present invention exist. One such class is for the absorption of medium to high menstrual flows. These sanitary napkins offer a fairly high absorptive capacity. Absorptive capacity is commonly achieved by providing the napkin with a fairly thick and bulky absorbent member, commonly fluff pulp. Sanitary napkins of this class are disclosed in U.S. Pat. No. 3,294,091 which issued to Morse on Dec. 27, 1966 and U.S. Pat. No. 4,654,040 which patent issued to Luceri on Mar. 31, 1987.

Such sanitary napkins theoretically have a high absorptive capacity, however, when the sanitary napkin is worn and subjected to the compressive forces of the wearer's thighs and pudendal region, the fluff pulp core simply compacts or bunches into an arbitrary, but generally rope-like shape. Such napkins commonly shift from their original placement so that after only a short wearing time, the napkin might only partially, if at all, be beneath the wearer's vaginal orifice or vestibule. Thus, in use, these sanitary napkins sometimes offer very little absorption. Further, the rolling and twisting of these napkins may create soiling on the wearer's panties and skin surfaces. In addition, the bulkiness of these napkins causes a high degree of wearing awareness and may make them quite obtrusive when worn with tight fitting slacks, body suits or bathing suits.

A second class of sanitary napkins are intended for light or low menstrual flows and are commonly referred to as panty liners or panty shields. Sanitary napkins of this type are disclosed in U.S. Pat. No. 4,681,578, entitled "Pantiliner With Ventilation Areas", which patent issued to Anderson and Brandt on Jul. 21, 1987. Sanitary napkins of this class, as a group, are thinner, somewhat more flexible and generally more comfortable than those of the first class, however, they lack the absorptive capacity of the napkins of the first class.

Recently, efforts have also been directed at developing thin sanitary napkins which have the capacity to absorb and contain medium to high menstrual discharges. Previously, such discharges could only be handled by relatively thick sanitary napkins. Examples of thin sanitary napkins having capacities great enough to handle medium to high menstrual flows are disclosed in U.S. Pat. Nos. 4,950,264 and 5,009,653, issued to Osborn, III, on Aug. 21, 1990 and Apr. 23, 1991, respectively. The disclosures of both of these patents are incorporated by reference herein.

It is also desirable that sanitary napkins conform as closely as possible to the body of the wearer. Such a body-conforming capability is believed to increase the effectiveness of the sanitary napkin by reducing the possibility that menses will travel around the perimeter of the sanitary napkin and leak. There have been a number of recent efforts to provide sanitary napkins and other absorbent articles with improved body-conforming characteristics. In addition to serving as examples of thin sanitary napkins, the sanitary napkins disclosed in the above-mentioned Osborn patents also serve as examples of anatomically-conforming sanitary napkins. Other examples of anatomically-conforming sanitary napkins are disclosed in European Patent Application publication numbers 0 335 252 and 0 335 253 published Oct. 4, 1989 in the name of Kenneth Barclay Buell, which are also incorporated by reference herein.

One attempt to reduce the tendency of a thin sanitary napkin to twist and bunch during use is described in Kimberly-Clark European Patent Application Publication Number 0 471 114 A2 published Feb. 19, 1992. This publication is also incorporated by reference herein. The Kimberly-Clark European Patent Application discloses providing a thin sanitary napkin with a thin "central zone" that has greater stiffness than adjacent portions of the napkin.

While the sanitary napkins disclosed in the Osborn patents and the Buell patent applications work quite well, the search for improved sanitary napkins has continued.

Therefore, there exists a real consumer need for a sanitary napkin which is generally thin and flexible, thereby offering enhanced fit and comfort, yet having a fluid capacity great enough for use with medium to high menstrual flows. The present application is directed to a number of such sanitary napkin embodiments.

It is an object of the present invention to provide a sanitary napkin which is generally thin and flexible and which is absorbent enough to absorb and contain medium to high menstrual flows.

It is an additional object of the present invention to provide a sanitary napkin which will closely conform to the various anatomical shapes of the female urogenital region, and, in particular, will easily form around the curvature of the wearer's labia majora by cupping and surrounding the exterior of the labia majora.

It is an additional object of the present invention to provide a sanitary napkin which offers enhanced fit and comfort and a low degree of wearing awareness.

These and other objects of the present invention will be more readily apparent when considered in reference to the following description and when taken in conjunction with the accompanying drawings.

SUMMARY OF THE INVENTION

The present invention is an absorbent article, such as a sanitary napkin. The sanitary napkin of the present invention is a generally thin, flexible, sanitary napkin that is provided with stiffened center.

The sanitary napkin of the present invention has a principal longitudinal centerline, a transverse centerline, a body surface, and a garment surface. A longitudinal central region is disposed along the length of at least a portion of the longitudinal centerline, and longitudinal side regions are disposed outboard of the longitudinal central region. The sanitary napkin comprises a liquid pervious topsheet, a liquid impervious backsheet (or "barrier means") joined to the topsheet, and an absorbent core positioned between the topsheet and backsheet. In one preferred embodiment shown in the drawings, the sanitary napkin is provided with a liquid permeable wipe acquisition sheet and a wet-laid tissue sheet, which together with the topsheet and absorbent core are said to comprise an "absorbent means".

The sanitary napkin has flexure-resistances in its longitudinal side regions and longitudinal central region that are within certain ranges. The longitudinal central region of the sanitary napkin has a flexure-resistance that is greater than that of the longitudinal side regions when measured according to the Circular Bend Procedure described in greater detail herein. The longitudinal central region preferably has a flexure-resistance of less than about 1,000 grams. The longitudinal side regions preferably have flexure resistances of less than or equal to about 700 grams (provided, of course, that the flexure-resistance of the longitudinal central region is always greater than the flexure-resistance of the longitudinal side regions.)

The embodiment of the sanitary napkin described above easily forms around the curvature of the wearer's labia majora by cupping and surrounding the exterior of the labia majora. The longitudinal central region of the sanitary napkin forms the bottom of a cup-like trough under the wearer's labia majora, and the longitudinal side regions are sufficiently flexible that they are able to form the sides of the trough structure.

In another embodiment, the sanitary napkin has a first end region extending between about ⅛ and ⅓ of the length of the sanitary napkin from one end edge of the sanitary napkin toward the transverse centerline, a second end region extending between about ⅛ and ⅓ of the length of the sanitary napkin from the other end edge toward the transverse centerline, and a central region that may range in width up to the width of the absorbent core between the first and second end regions. This sanitary napkin has a flexure resistance as measured through the first and second end regions which is less than the flexure resistance as measured through the central region.

DETAILED DESCRIPTION OF PREFERRED EMBODIMENTS

The present invention relates to absorbent articles, such as sanitary napkins, and in particular to sanitary napkins which are generally thin and flexible that are provided with a stiffened center and offer enhanced fit, comfort, and containment.

The term "sanitary napkin", as used herein, refers to an article which is worn by females adjacent to the pudendal region and which is intended to absorb and contain the various exudates which are discharged from the body (e.g., blood, menses and urine) and which is intended to be discarded after a single use (i.e., it is not intended to be laundered or otherwise restored or reused). Interlabial devices which reside partially within and partially external of the wearer's vestibule are also within the scope of this invention. As used herein, the term "pudendal" refers to the externally visible female genitalia and is limited to the labia majora, the labia minora, the clitoris, and the vestibule.

Figure 1:
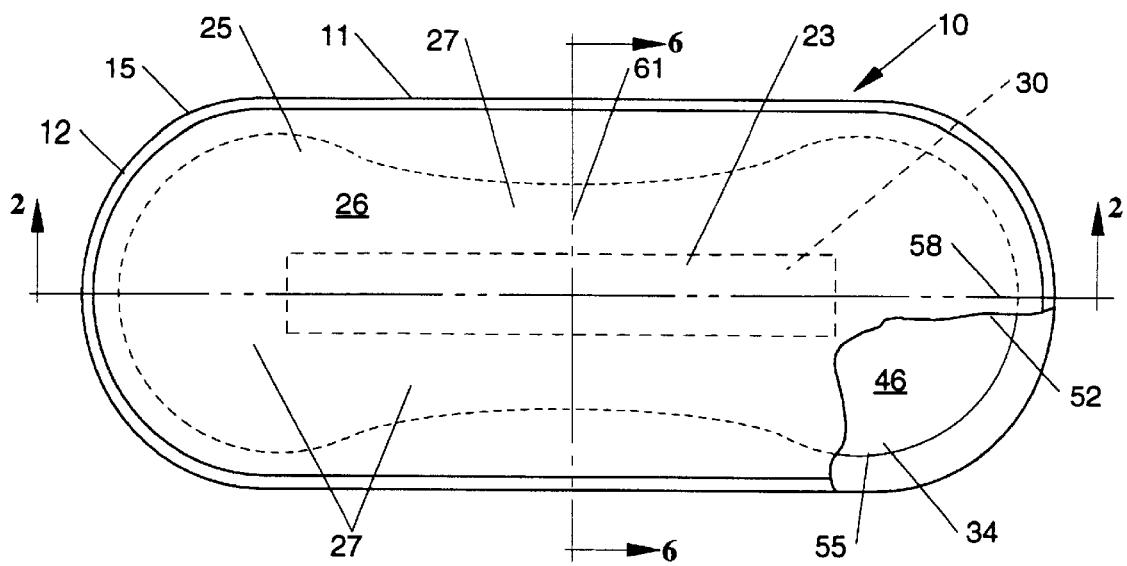
FIG. 1 is a schematic plan view of a sanitary napkin of the present invention with portions being torn away to show underlying structure.
Figure 2:
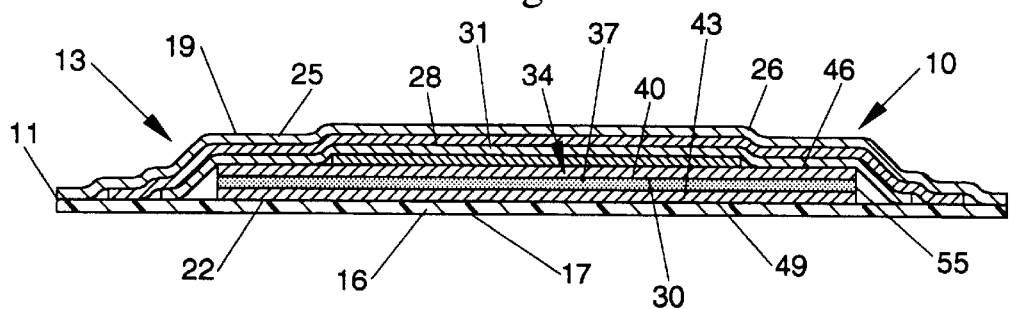
FIG. 2 is a cross-sectional view of the sanitary napkin shown in FIG. 1 taken along line 2—2 of FIG. 1.

FIGS. 1 and 2 are a schematic plan view and a cross-sectional view of one embodiment of the sanitary napkin 10 of the present invention. As can be seen in FIGS. 1 and 2, the sanitary napkin 10 basically comprises an absorbent means 13 and a liquid impermeable barrier means 16. The absorbent means 13 may be any means which is generally compressible, conformable, non-irritating to the wearer's skin and capable of absorbing and containing body exudates such as menses, blood and urine. Preferably, the absorbent means 13 maintains integrity when wetted, in use. The absorbent means 13 has a first major surface 19 and a second major surface 22. The barrier means 16 is adjacent the second major surface 22 of the absorbent means 13. The barrier means 16 may be any means which is flexible and liquid impervious and which prevents the exudates absorbed and contained in the absorbent means 13 from wetting articles which contact the sanitary napkin 10 such as panties.

As shown in FIGS. 1 and 2, the absorbent means 13 is comprised of a liquid permeable topsheet 25, a liquid permeable wipe acquisition sheet 28, a wet-laid tissue sheet 31 and an absorbent core 34. In the embodiment shown in FIGS. 1 and 2, the barrier means 16 is a barrier sheet. The absorbent core 34 is comprised of hydrogel-forming material 37 disposed between two air-laid tissue sheets 40 and 43. The sanitary napkin 10 has side edges 11 and end edges 12 which together form the periphery 15 of the sanitary napkin 10. The sanitary napkin 10 has a body surface 26 which is generally defined by the topsheet 25 and a garment surface 17 which is generally defined by the barrier sheet 16.

The sanitary napkin 10 has a longitudinal central region 23 disposed along the length of at least a portion of the longitudinal centerline 58 (and preferably centered about the same). The size and shape of longitudinal central region 23, may vary depending upon the structure that provides the sanitary napkin with a stiffened longitudinal central region (or "stiffened center"). The sanitary napkin 10 can be provided with a stiffened center in a number of different ways.

Some general ways of providing the sanitary napkin 10 with a stiffened longitudinal central region include, but are not limited to: (1) making the longitudinal central region 23 thicker; (2) folding any of the components comprising the longitudinal central region to create double, or more, thickness of the same; (3) constructing the longitudinal central region out of several layers; (4) using stiffer materials; (5) changing the basis weight of components comprising the longitudinal central region; (6) placing additional components in the longitudinal central region 23; or (7) any combinations of the foregoing.

Several specific non-limiting sanitary napkin embodiments with a stiffened center are shown in FIGS. 6–23.

Figure 6:
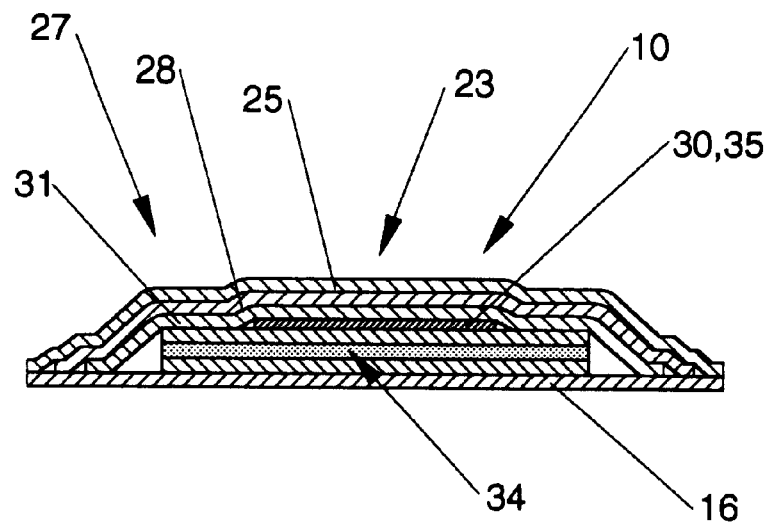
FIG. 6 is a cross-sectional view of a sanitary napkin having a stiffening material in the form of an additional absorbent material placed in the longitudinal central region of the sanitary napkin.

FIG. 6 shows a sanitary napkin 10 having a stiffening element (or "stiffening material") 30 in the form of an additional absorbent material 35 placed in the longitudinal central region 23. The additional absorbent material 35 could comprise any of the materials specified herein as being suitable for use in the absorbent core 34. The additional absorbent material 35 could also comprise capillary channel fibers (described in greater detail below), or cross-linked cellulose fibers. Suitable cross-linked cellulose fibers are described in U.S. Pat. No. 4,888,093, issued Dec. 19, 1989 to Cook et al.; U.S. Pat. No. 4,822,543, issued Apr. 18, 1989 to Dean, et al.; U.S. Pat. No. 4,889,559, issued Dec. 26, 1989 to Schoggen, et al.,; U.S. Pat. No. 4,898,642, issued Feb. 6, 1990 to Moore, et al.; and U.S. Pat. No. 4,935,022 issued Jun. 19, 1990 to Lash et al.

The additional absorbent material 35 could be in any suitable form, including, but not limited to masses or wads of material, single unfolded sheets, folded sheets, strips of material, loose or bonded fibers, multiple layers or laminates of material, or other combinations of such material. The additional absorbent material 35 could be positioned between any of the components between the topsheet 25 and the backsheet 16.

The stiffening material 30 could, for instance, comprise polymeric gelling agents added or patterned into the longitudinal central region 23. In other alternatives, the stiffening material could include, but not be limited to combinations of polymeric gelling agents and synthetic fibers, natural fibers, or chemically modified natural fibers, such as cross-linked cellulose fibers. In still other alternatives, suitable absorbent fibers such as chemically modified natural fibers may be used as the stiffening material without the addition of polymeric gelling agents.

One preferred type of stiffening material is a bi-component fibrous material comprising a fiber having a core of polyethylene which is coated with polypropylene. The outside of the bi-component fibers have a lower melting temperature than the inside. Such a material is preferred because the fibers can be heat bonded to each other by melting the outside of the fibers while the inside of the fibers maintain their fibrous integrity instead of melting into an amorphous mass.

Suitable bi-component fibers are commercially available from a company by the name of Chisso. Another material which is suitable for use as the stiffening material is a fibrous material known as PULPEX, formerly available from Hercules, Inc. of Wilmington, Del.

The stiffening material 30 such as additional absorbent material 35 could be used with the other components described herein, as shown in FIG. 6. Alternatively, it could replace one or more of the other components. In still other alternative embodiments, the stiffening material could be an integral part of the absorbent core 34 or one or more of the other components described herein.

Figure 7:
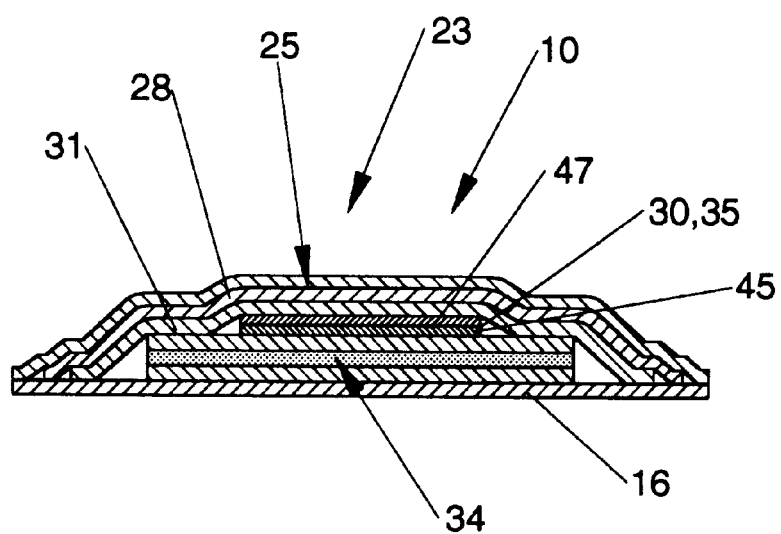
FIG. 7 is a cross-sectional view of a sanitary napkin provided with additional absorbent material in the form of a laminate.
Figure 8:
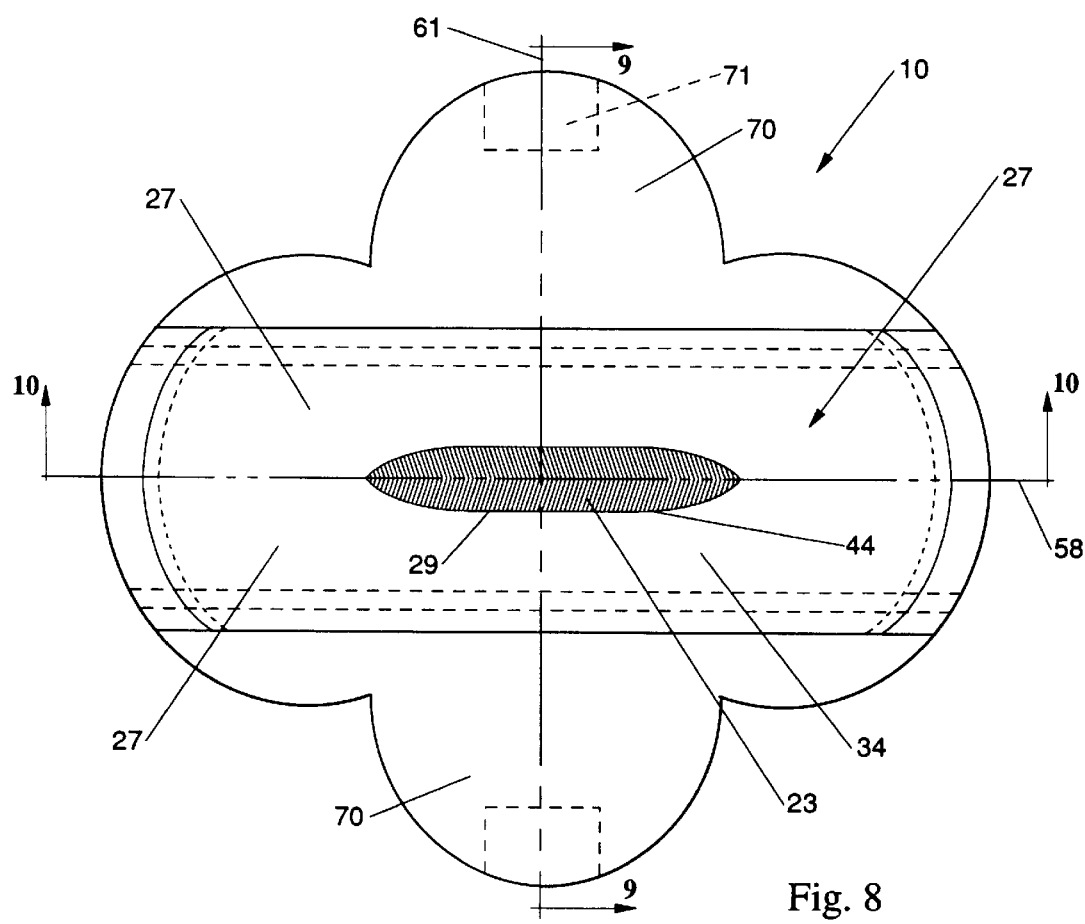
FIGS. 8–12 show a sanitary napkin provided with additional absorbent material in the form of a longitudinally-oriented hump.

FIG. 7 shows a sanitary napkin 10 provided with additional absorbent material 35 in the form of a laminate. The laminate comprises an additional layer of hydrogel-forming material 45 and an additional tissue layer 47.

FIGS. 8–12 show a sanitary napkin 10 provided with a longitudinally-oriented absorbent hump 44. The hump 44 comprises additional absorbent material in the form of a hump-forming element 44'. The absorbent hump 44 provides extra absorbency in the target region where menses are typically deposited and improved contact with the wearer's body, particularly with the surfaces of the wearer's labia majora adjacent the space between the labia majora.

The sanitary napkin shown in 8–12 preferably has longitudinal side regions 27 with a caliper of less than or equal to about 5 millimeters. The sanitary napkin 10 preferably has a caliper at the point of maximum amplitude of the hump 44 of at least about 150% of the caliper of the longitudinal side regions 27. The sanitary napkin preferably has a caliper as measured through the point of maximum amplitude of the hump 44 that is at least about 0.15 inch (about 3.5–4 millimeters), more preferably between about 4 millimeters and about 10 millimeters greater than that of the longitudinal side regions 27.

Figure 9:
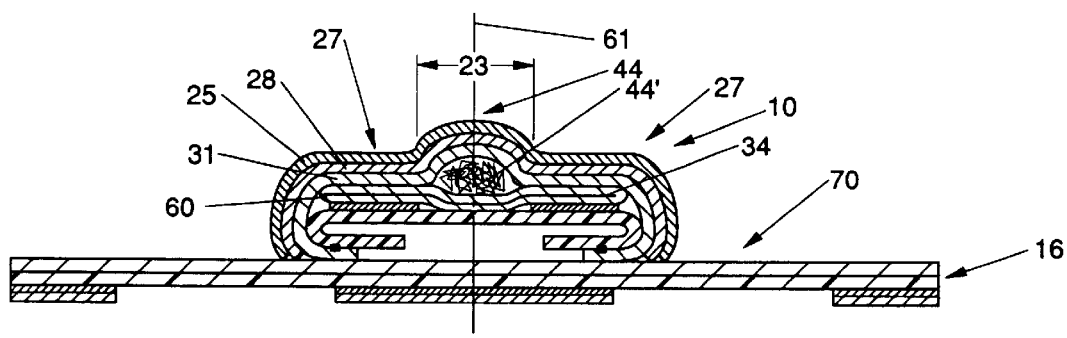
Figure 10:
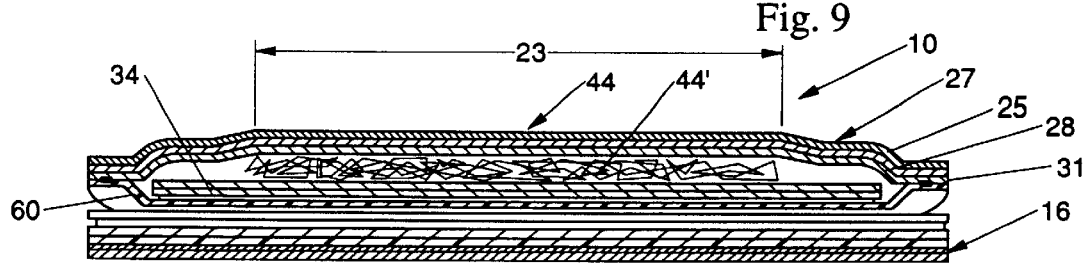

The sanitary napkin shown in FIGS. 8–12 can be provided with an optional interliner 60 as shown in FIGS. 9 and 10. FIGS. 9 and 10 are sectional views taken along lines 9—9 and 10—10, respectively, of the plan view shown in FIG. 8. The optional interliner 60 is used when the sanitary napkin is provided with an absorbent core 34 that has the ability to separate or "decouple" from the backsheet 16 for improved body contact. The concept of decoupling and the characteristics of the interliner are described in U.S. Pat. No. 5,007,906 issued to Osborn, et al. on Apr. 16, 1991 which is incorporated by reference herein.

Figure 11:
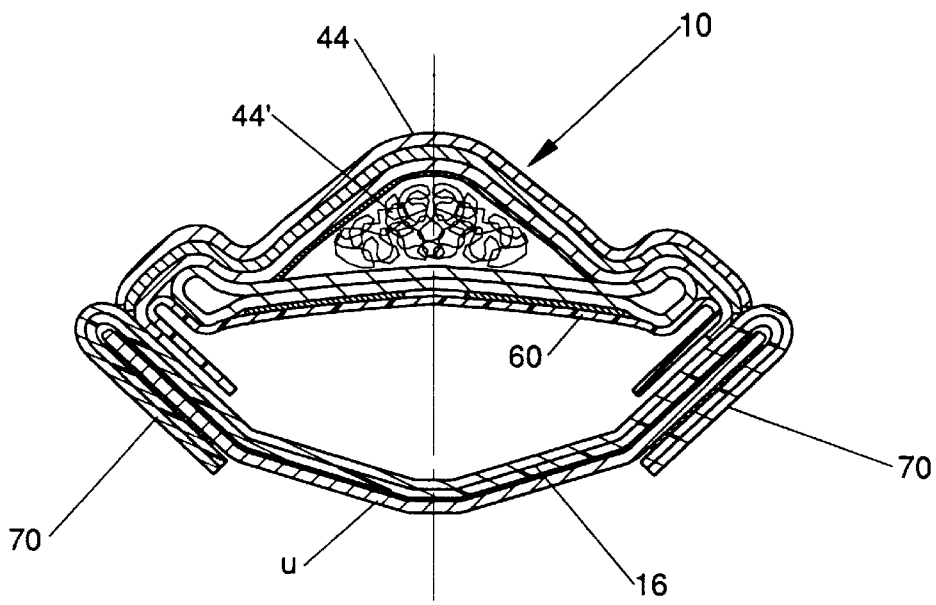
Figure 12:
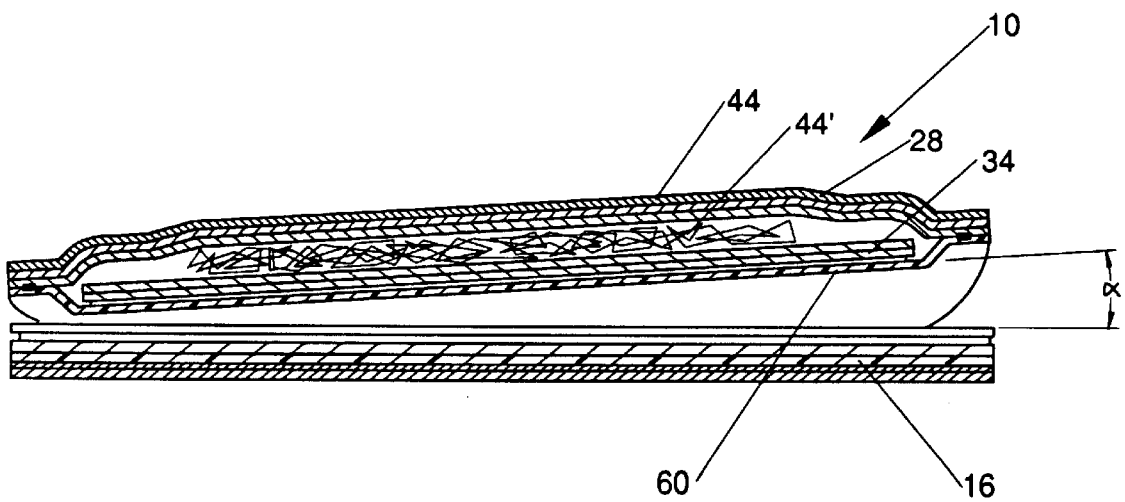

FIGS. 11 and 12 are sectional views taken from similar angles to FIGS. 9 and 10, respectively. FIGS. 11 and 12 show examples of possible configurations the sanitary napkin 10 shown in FIGS. 8–10 might take when the absorbent core 34 decouples from the backsheet 16. It should be understood, however, that the sanitary napkins shown in the drawing figures are shown primarily for purposes of illustration. The sanitary napkins may assume other configurations when worn. It should also be understood that the sanitary napkins are not necessarily drawn to scale.

FIGS. 13–18 show a sanitary napkin 10 provided with additional absorbent material in the form of a longitudinally oriented absorbent mass 48 which is capable of decoupling from the absorbent core 34. The views of the sanitary napkin 10 shown in FIGS. 13–17 are similar to those of the previous embodiment.

The absorbent mass 48 is located under the body surface 26 of the sanitary napkin 10. The absorbent mass 48 is capable of moving apart from the main absorbent component(s), such as the absorbent core 34, of the sanitary napkin to more readily intercept bodily discharges when they leave the body.

Figure 18:
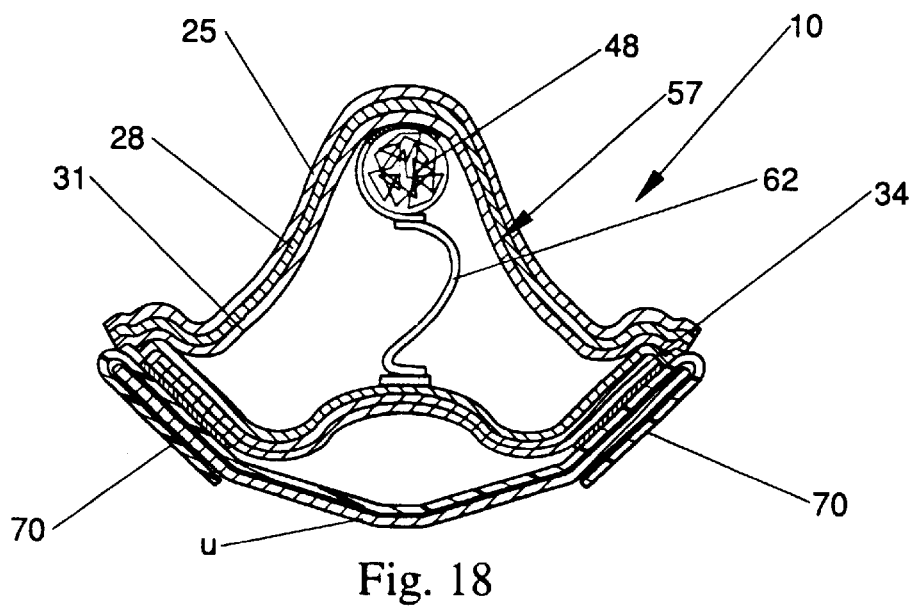

The absorbent mass 48 is preferably elongated longitudinally-oriented, readily deformable, and resilient absorbent mass 48 is positioned between the topsheet 25 and the absorbent core 34. Preferably, at least one absorbent layer 57 is positioned between the topsheet 25 and the absorbent mass 48. FIG. 18 shows at least one absorbent layer 57 which comprises a wipe acquisition sheet 28 and a wet-laid tissue sheet 31.

The absorbent mass 48 is preferably joined to the topsheet 25 (either directly or indirectly (for example, through the absorbent layer 57). The absorbent mass 48 shown in FIGS. 13–17 is unsecured to the absorbent core 34. The absorbent mass 48 may move apart from the absorbent core 34 in conjunction with at least a portion of the topsheet 25. This provides the sanitary napkin with an absorbent component that can move into close proximity to the wearer's body independently of the other absorbent components of the sanitary napkin 10.

Figure 13:
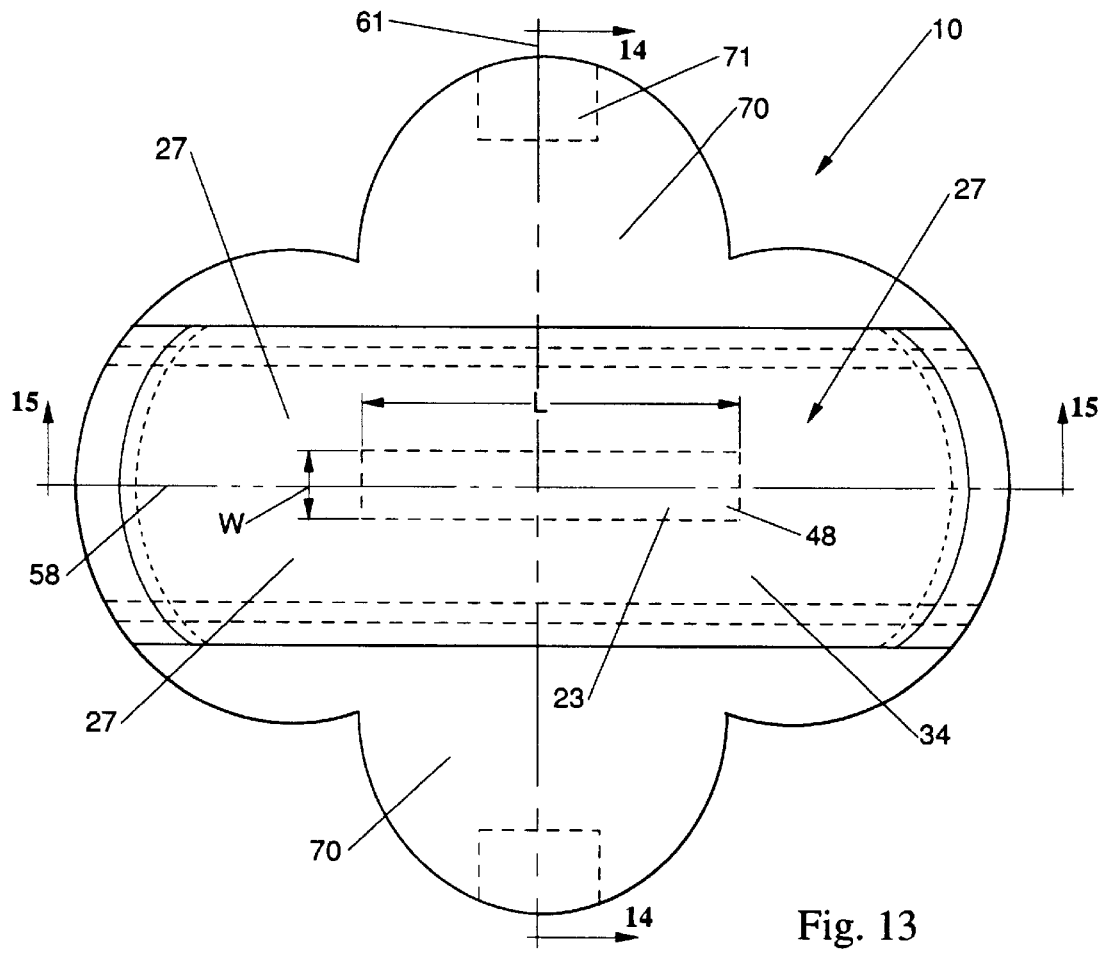
FIGS. 13–18 show a sanitary napkin provided with additional absorbent material in the form of an absorbent mass which is capable of decoupling from the absorbent core.
Figure 14:
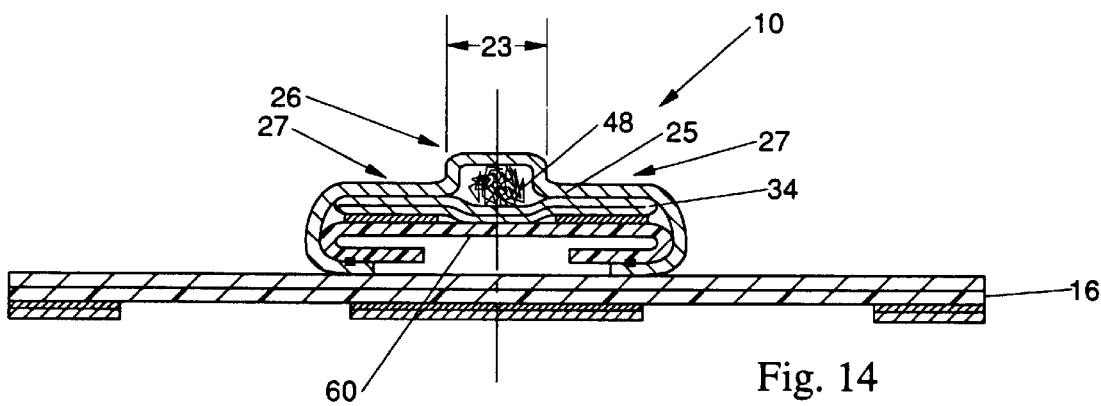
Figure 15:
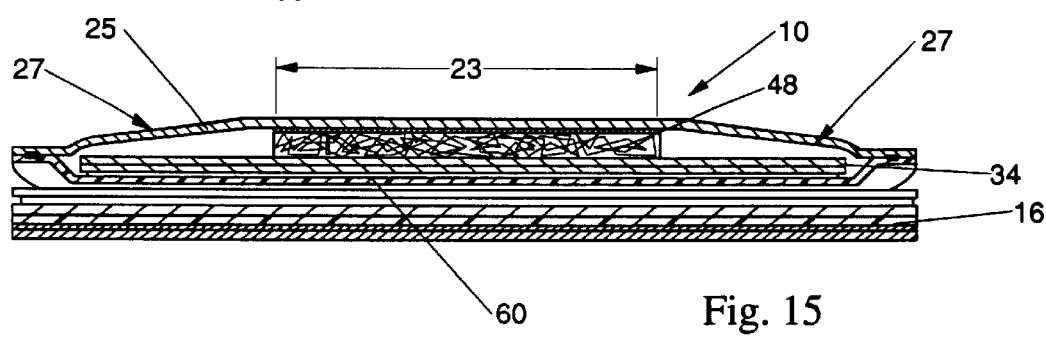
Figure 16:
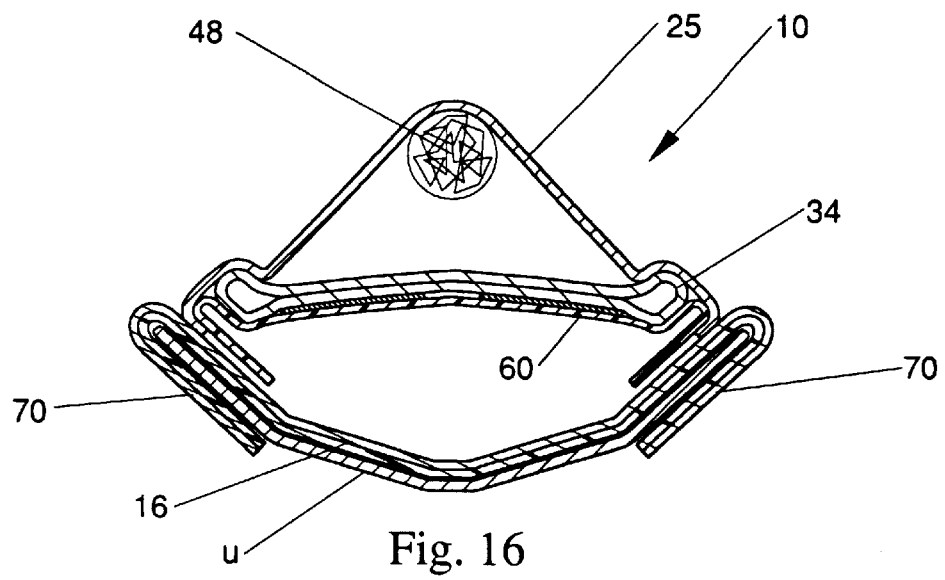
Figure 17:
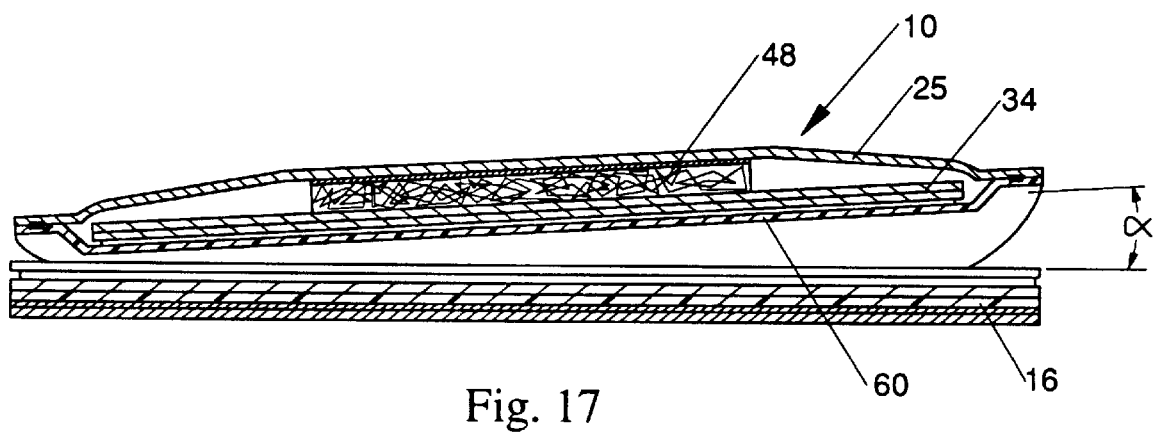

This embodiment can also be provided with an absorbent core 34 capable of decoupling from the backsheet 16. FIGS. 13–14 show the sanitary napkin prior to decoupling. FIGS. 16 and 17 show possible configurations of the sanitary napkin might take when the absorbent core 34 decouples from the backsheet 16.

FIG. 18 is taken from an angle similar to that of FIG. 16. FIG. 18 shows an embodiment in which the absorbent mass 48 is joined to the absorbent core 34 by flaccid fluid transporting material 62. Fluids initially absorbed by the absorbent mass 48 may be transported from the absorbent mass 48 to the absorbent core 34 by way of the fluid transporting material 62.

Figure 19:
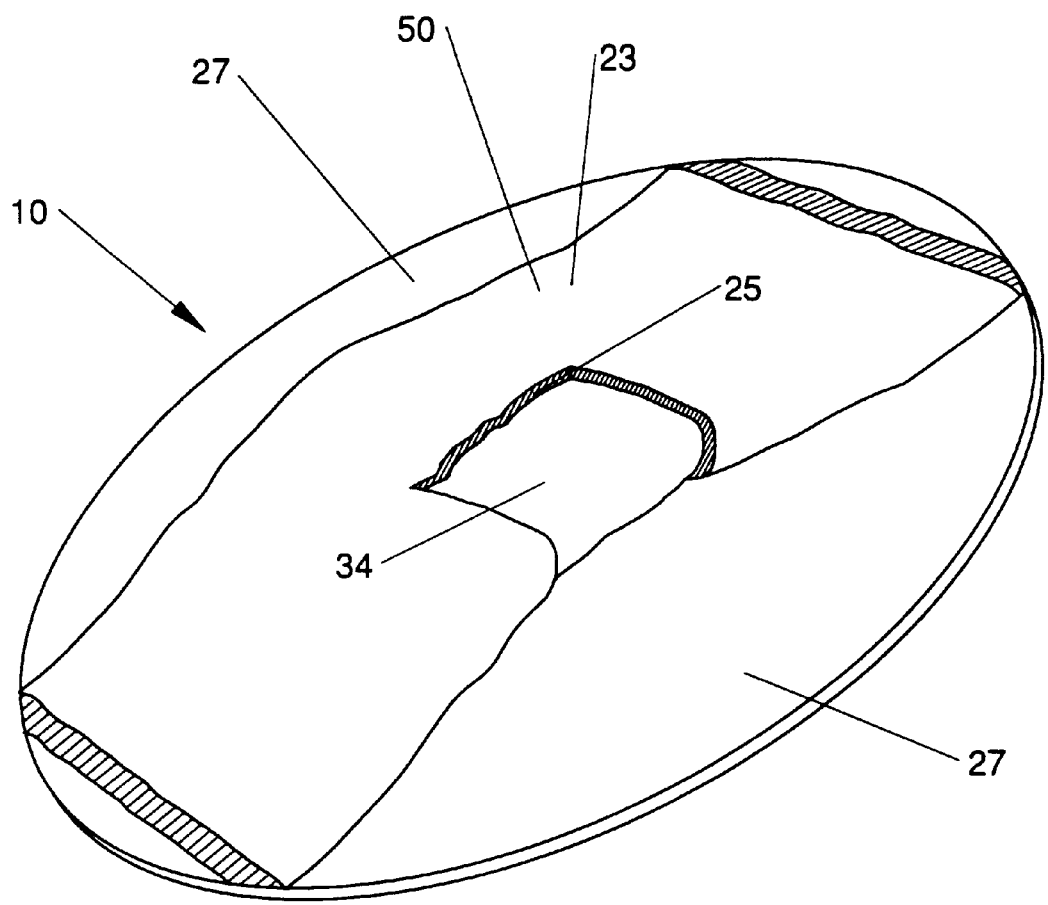
FIG. 19 is a perspective view of a sanitary napkin provided with a longitudinally oriented absorbent tube capable of decoupling from a panty protector.

FIG. 19 shows a sanitary napkin 10 having another type of stiffening element. The sanitary napkin 10 shown in FIG. 19 is provided with a longitudinally-oriented absorbent tube that provides the sanitary napkin 10 with a detached thick center (or "primary menstrual pad") 50. The sanitary napkin 10 could be constructed generally in accordance with the disclosure of U.S. Pat. No. 4,425,130 issued to DesMarias on Jan. 10, 1984. However, the dimensions of the primary menstrual pad 50, and the stiffness of the central region 23 and the longitudinal side regions 27 should be within the limits described in this specification. Thus, although the detached thick center 50 is shown as extending the length of the sanitary napkin 10, it may only extend a portion of the length of the sanitary napkin 10.

Figure 20:
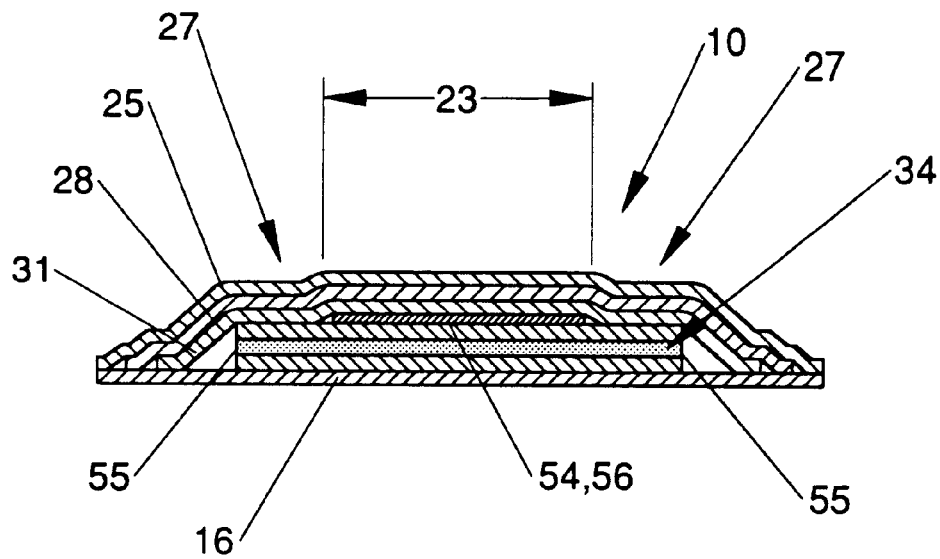
FIGS. 20 and 21 are cross-sectional views of sanitary napkins provided with stiffening material in the form a non-absorbent film and a construction adhesive, respectively.

FIG. 20 shows a sanitary napkin 10 provided with a non-absorbent stiffening material 54. The stiffening material 54 could be: non-absorbent and pervious; non-absorbent and impervious; or non-absorbent and an inherently impervious material but apertured, slit, or the like to make the element itself pervious. The non-absorbent stiffening material 54 could comprise any suitable material. For instance, the non-absorbent stiffening material 54 could comprise a foam insert, or a strip of plastic film 56. The plastic film 56, as noted above, could be impervious and either apertured or unapertured.

The strip of film 56 may be used to direct exudates toward the ends of the core 34. Liquid exudates that are deposited on the core 34 will tend to be distributed radially outward from the place where they are deposited. Since the core 34 of the sanitary napkin 10 is relatively narrow in comparison to its length, liquid exudates will reach the longitudinal edges 55 of the core 34 much sooner than they will reach the ends of the absorbent core 34. The strip of film 56 can be used to longitudinally wick and direct exudates toward the ends of the core 34. This more effectively utilizes the capacity of the core, and reduces the possibility of leakage caused by exudates prematurely reaching the longitudinal edges 55 of the core 34.

Figure 21:
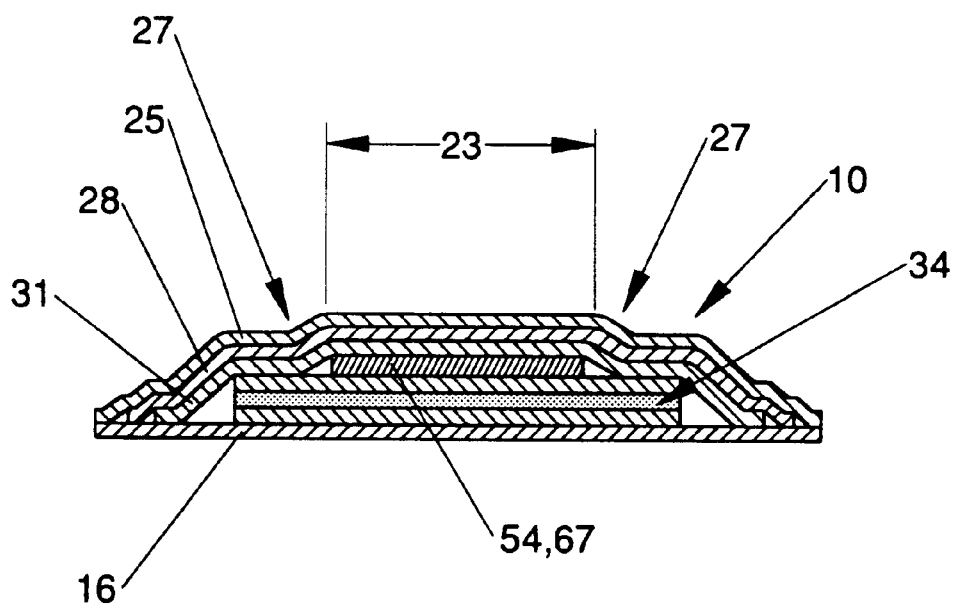

FIG. 21 shows an alternative embodiment in which the non-absorbent stiffening material 54 comprises an adhesive 67 used in the construction of the sanitary napkin 10. The adhesive 67 shown in FIG. 21 is between the wet-laid tissue 31 and the absorbent core 34. The adhesive 67 can, alternatively or additionally, be between the absorbent core 34 and the backsheet 16, between the layers of the absorbent core 34, between the absorbent core 34 and the topsheet 25, or between any of the other components described herein.

Figure 22:
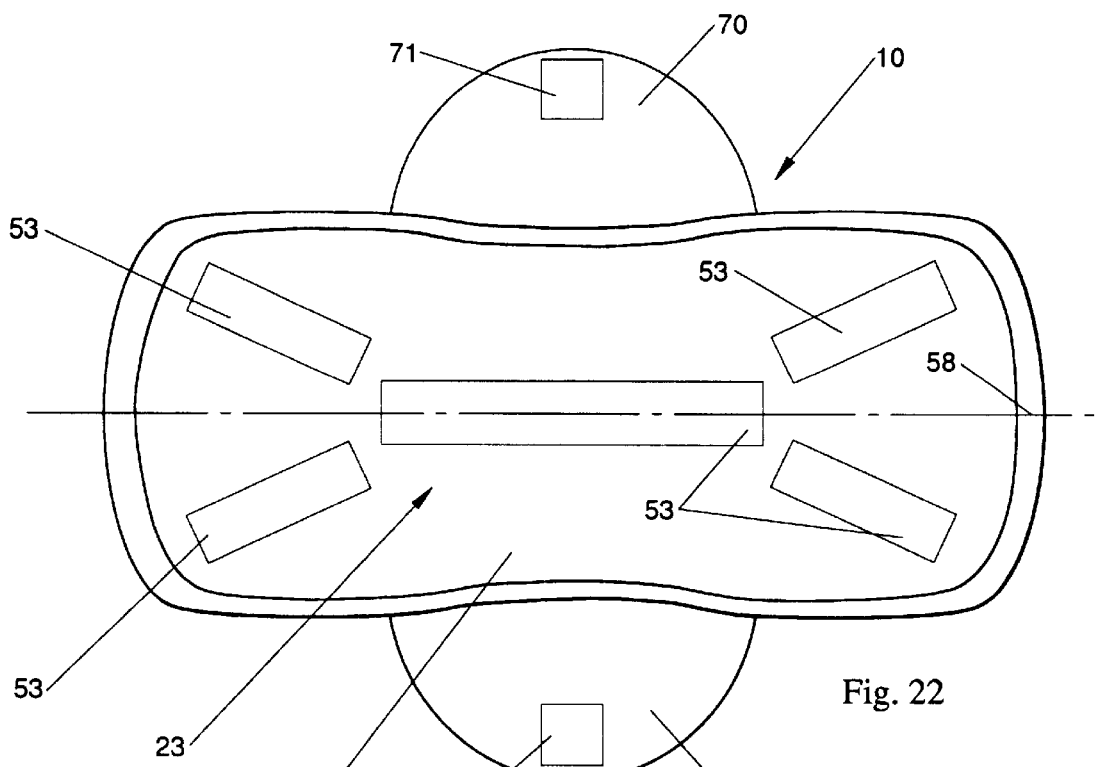
FIGS. 22 and 23 are bottom plan views of sanitary napkins that have fasteners which provide the napkins with a stiffened center.
Figure 23:
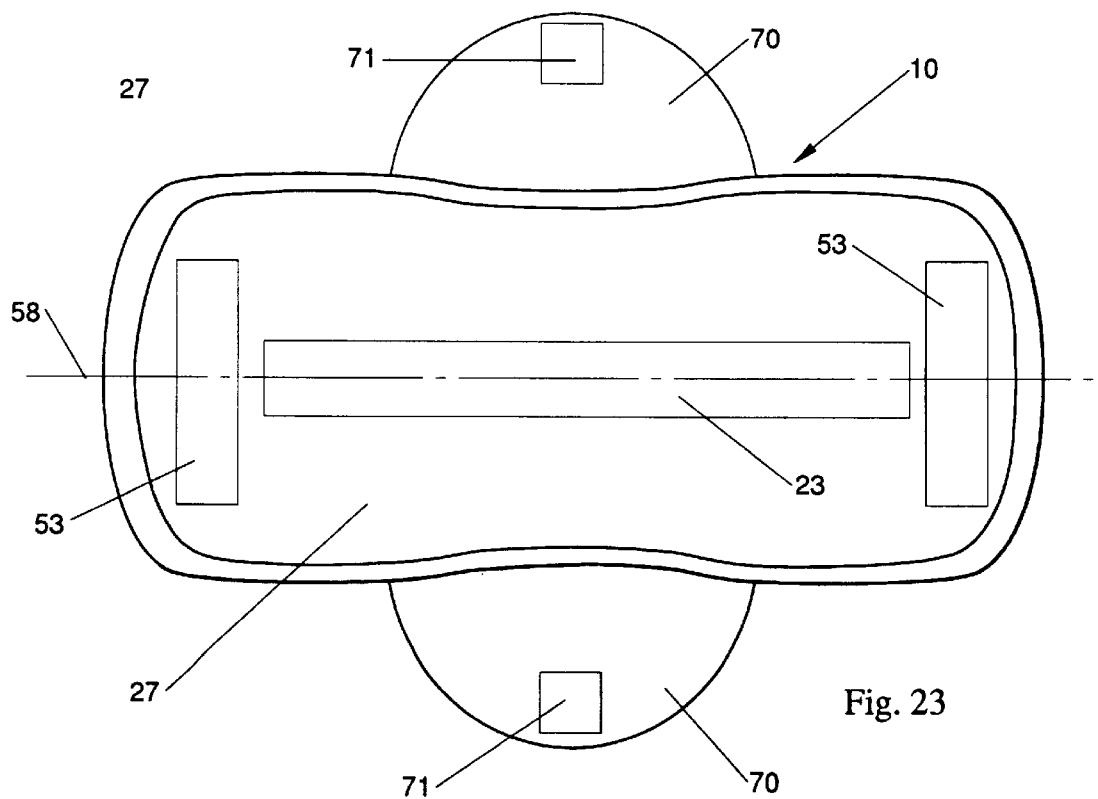

FIGS. 22 and 23 show two sanitary napkins 10 that are provided with fasteners, such as panty fasteners, 53 that give the napkins a stiffened center. The fasteners may provide the sanitary napkin 10 with a stiffened center either by being inherently stiff, or by securing the longitudinal central region 23 of the sanitary napkin to the wearer's panties in such a way that the longitudinal central region 23 is not able to separate from the panties and flex as much as the surrounding longitudinal side regions 27. The fasteners 53 could be any suitable type of fastening device including, but not limited to adhesives, hook material such as that used in Velcro fasteners, or any other suitable type of fastener such as that described in U.S. Pat. No. 4,946,527 issued to Battrell on Aug. 7, 1990.

The length l of the longitudinal central region 23 can range from between about 0.75 inch (about 2 cm.) to the length of the absorbent core 34. (The length of the absorbent core 34 can, for example, be about 8.5 inches (about 22 cm.). Preferably, the length l of the longitudinal central region 23 is between about 1.5 inches (about 4 cm.) and about 6 inches (about 15 cm.), and more preferably, is between about 1.5 inches (about 4 cm.) and about 4 inches (about 10 cm.), and most preferably is between about 1.5 inches (about 4 cm.) and about 3 inches (about 7.5 cm.).

The width w of the longitudinal central region 23 in the embodiments shown in FIGS. 6–23 may be as great as between about ¼ inch (about 0.5 cm.) and about 2 inches (about 5 cm.). Preferably, the width w of the longitudinal central region 23 is between about ⅜ inch (about 1 cm.) and about 2 inches (about 5 cm.), and more preferably is between about ⅜ inch (about 1 cm.) and about 1 ¾ inches (about 4.5 cm.), and most preferably is between about ⅜ inch (about 1 cm.) and about 2 inch (about 4 cm.).

The longitudinal side regions (or "side regions") 27 are the significant absorbent portions that lie outboard of the longitudinal central region 23. The term "outboard" means positioned away from the intersection of the longitudinal and transverse centerlines, 58 and 61. The longitudinal side regions 27 will typically lie at least transversely (i.e., laterally) outboard of the longitudinal central region 23 so that they are on the longitudinal sides of the longitudinal central region 23 and the sanitary napkin 10 (hence the name "longitudinal side regions").

The longitudinal side regions 27 can, however, lie outboard of the longitudinal central region 23 in either a longitudinal direction (i.e., outside the ends of the longitudinal central region 23), a transverse direction (i.e., outside the longitudinal edges of the longitudinal central region 23, or both (the latter being shown in FIG. 1). The longitudinal side regions 27 should have some capacity, preferably they have a capacity of at least about 1 gram.

The sanitary napkin 10 is said to be "generally" thin and flexible. When the sanitary napkin 10 is described in this manner, it is meant that the longitudinal side regions 27 of the sanitary napkin are relatively thin and flexible though the longitudinal central region 23 may be relatively thick and inflexible, or merely relatively inflexible or relatively thick and inflexible in comparison to the longitudinal side regions 27. The embodiment of the sanitary napkins 10 shown the drawings are intended to be examples of generally thin sanitary napkins. However, it should be understood when viewing the drawings, the number of layers of material shown may cause the sanitary napkins to appear much thicker than they actually are.

The flexibility of the different regions of the sanitary napkin 10 is probably best understood with reference to FIGS. 24–28.

Figure 24:
FIG. 24 is a schematic cross-sectional view showing the way a prior art sanitary napkin might fit adjacent the wearer's labia designated L.

FIG. 24 shows one possible configuration that the prior art uniformly thin sanitary napkins such as those described in U.S. Pat. Nos. 4,950,264 and 5,009,653 issued to Osborn might take when worn. The wearer's labia is represented in the drawings by the letter L. Again, the drawings are not necessarily to scale, and it is to be understood that the sanitary napkings may not necessarily take these configurations in all cases.

Figure 25:
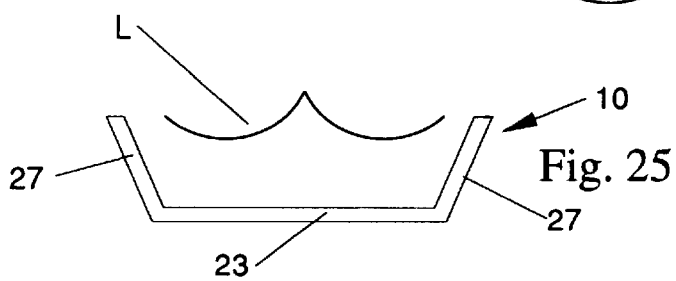
FIG. 25 is a schematic cross-sectional view showing the way a sanitary napkin having a stiffened center might fit adjacent the wearer's labia.
Figure 26:
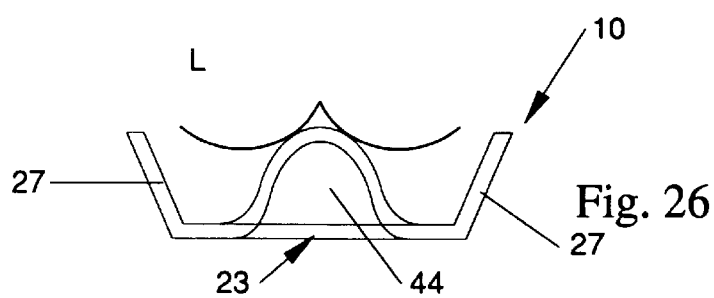
FIG. 26 is a schematic cross-sectional view showing the way a sanitary napkin having a stiffened center in the form of longitudinally-oriented hump might fit adjacent the wearer's labia.

The flexibility of the longitudinal side regions 27 of the sanitary napkin embodiments described above allows these regions to conform to the various shapes of the female urogenital region. As shown in FIG. 25, the longitudinal central region 23 will ideally be of such dimensions that it may fit adjacent the wearer's labia without being provided with the same degree of flexibility as the longitudinal side regions 27. FIG. 26 shows a configuration the sanitary napkin 10 having the hump 44 described with reference to FIGS. 8–12 might taken when worn.

Figure 27:
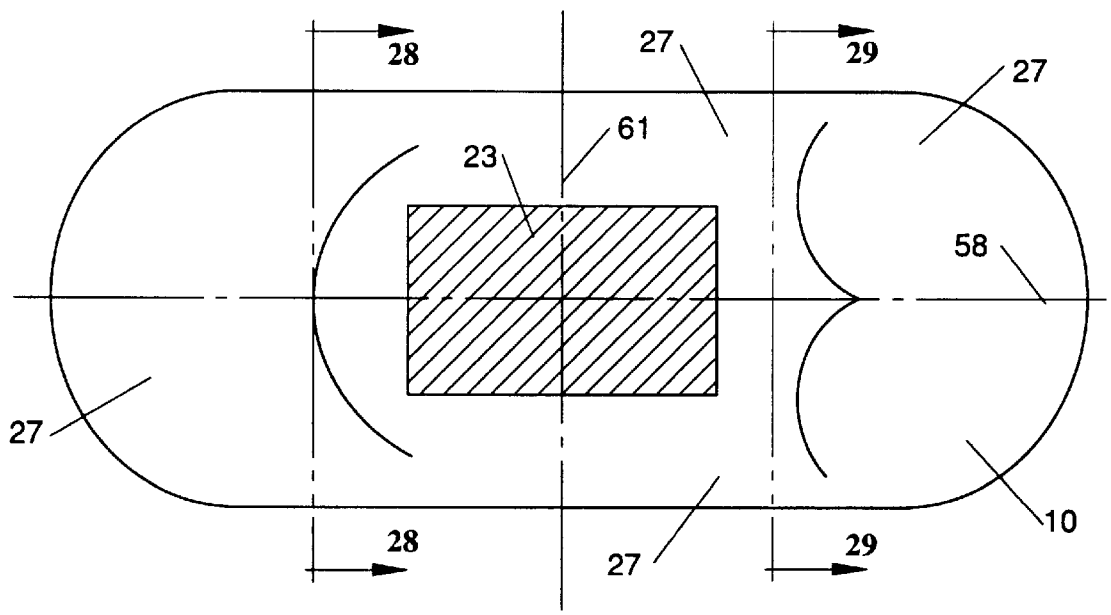
FIG. 27 is a schematic plan view showing the way the entire sanitary napkin might fit adjacent different regions of the wearer's body.

FIG. 27 shows that a sanitary napkin 10 in which the longitudinal central region 23 does not extend the length of the sanitary napkin 10 might take a number of different cross-sectional configurations when it is worn depending on the place along the length of the sanitary napkin 10 along which the cross-section is taken. The sanitary napkin 10 can adapt to three very distinct shapes of the wearer's body. From the front of the wearer's body to the back of the wearer's body, the first of the three regions may be thought of as the mons region having a compound curved convex upward shape. The second region is defined by the labia majora and resembles a W-shaped outline. The third region is determined by the gluteal groove and is generally cusp-shaped and defined by two convex upward and outwardly diverging lines.

Figure 28:
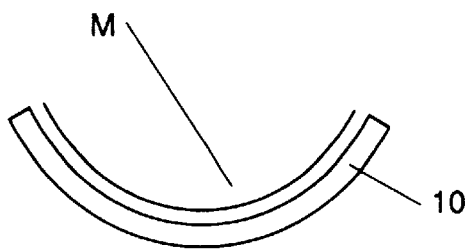
FIG. 28 is a schematic cross-sectional view showing the way a sanitary napkin of the present invention might fit adjacent the wearer's mons region.
Figure 29:
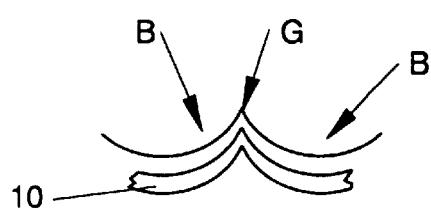
FIG. 29 is a schematic cross-sectional view showing the way a sanitary napkin of the present invention might fit in the crevice between the wearer's buttocks (or "gluteal groove").

FIG. 28 is a schematic cross-sectional view showing the way a sanitary napkin of the present invention might fit adjacent the wearer's mons region, M. FIG. 29 is a schematic cross-sectional view showing the way a sanitary napkin of the present invention might fit in the crevice between the wearer's buttocks B (or in the "gluteal groove") G.

The longitudinal central region 23 of the sanitary napkin 10 might fit adjacent the wearer's labia in either the configuration shown in FIG. 25 or FIG. 26, depending on whether sanitary napkin 10 is provided with a hump 44.

Figure 30:
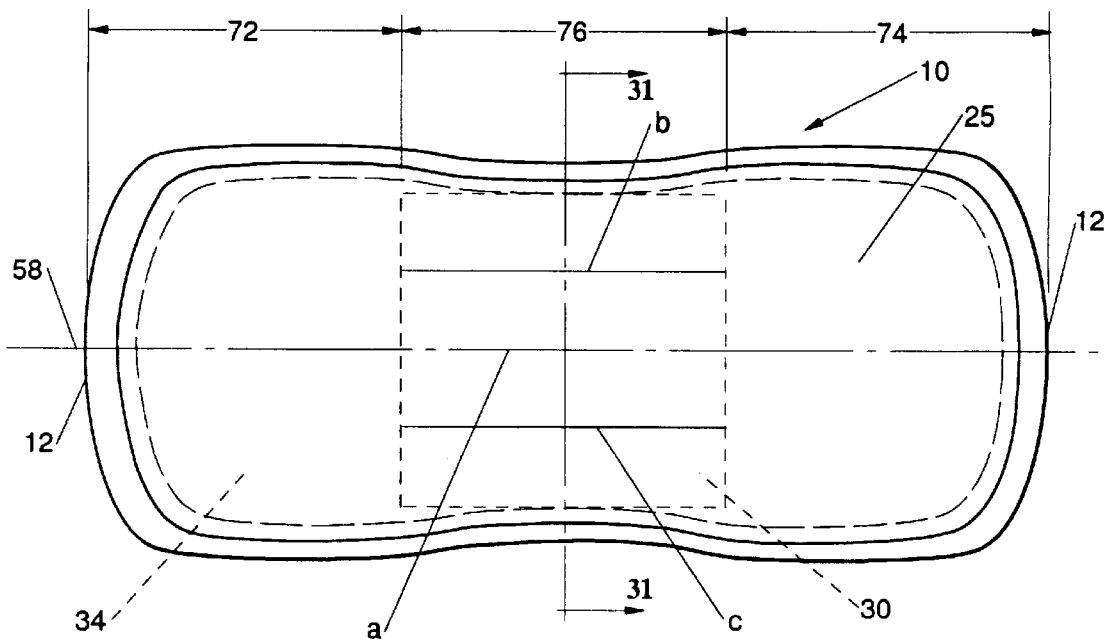
FIG. 30 is a schematic plan view of another sanitary napkin embodiment in which the sanitary napkin has a stiffened central region which may extend the full width of the absorbent core.

FIG. 30 shows an alternative sanitary napkin 10 embodiment of the present invention. The sanitary napkin 10 shown in FIG. 30 has a stiffened central region (or simply "central region") 76 that may extend up to the full width of the absorbent core 34.

The stiffened central region 76 may be provided by any suitable stiffening material 30 described herein. Preferably, however, an absorbent mass is not used for this purpose unless it tapers away from the longitudinal centerline 58 sufficiently that its size does not substantially inhibit the fit in space between the wearer's labia. Thus, if a mass of absorbent material is used, its caliper as measured more than one inch laterally outboard the longitudinal centerline 58 should preferably be within 1–2 mm. of that of the adjacent significant absorbent regions.

The sanitary napkin 10 shown in FIG. 30 has a first end region 72 extending between about ⅛ and ⅓ of the length of the sanitary napkin from one end edge 12 of the sanitary napkin toward the transverse centerline 61. The sanitary napkin 10 has a second end region 74 extending between about ⅛ and ⅓ of the length of the sanitary napkin from the other end edge 12 toward the transverse centerline 61. The central region 76 extends between the first and second end regions 72 and 74. This sanitary napkin 10 has a flexure resistance as measured through the first and second end regions 72 and 74 which is less than the flexure resistance as measured through the central region 76.

FIG. 30 shows that the sanitary napkin 10 may also be provided with optional score lines (or fold lines) a, b, and c. The optional score lines may be formed through a portion of the stiffening element 30, the entire sanitary napkin, or all or part of some of the other components of the sanitary napkin 10. FIGS. 31–34 show some possible configurations that the sanitary napkin 10 shown in FIG. 30 might take when it is worn.

Figure 31:
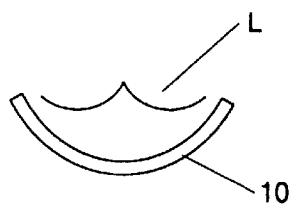
FIGS. 31–35 are schematic cross-sectional views which show the way different embodiments of the sanitary napkin shown in FIG. 30 might fit adjacent the wearer's labia.

FIG. 31 shows that a sanitary napkin 10 having a stiffened central region 76 without any score lines will generally forms a bow-like structure under the wearer's labia.

Figure 32:
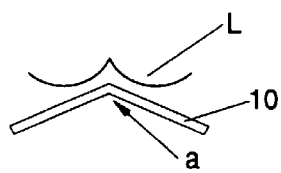

FIG. 32 shows that a sanitary napkin 10 having a stiffened central region 76 with a single fold line designated "a" that runs along the longitudinal centerline 58, and is predisposed to make the sanitary napkin bend upward into an inverted V-shaped configuration.

Figure 33:
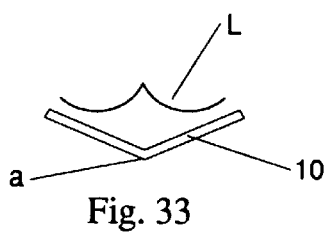

FIG. 33 shows that a sanitary napkin 10 having a stiffened central region 76 with a single fold line designated "a" that runs along the longitudinal centerline 58, and is predisposed to make the sanitary napkin bend downward into a V-shaped configuration.

Figure 34:
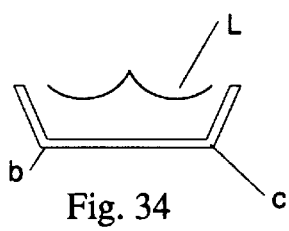

FIG. 34 shows that a sanitary napkin 10 having a stiffened central region 76 with a pair of fold lines, designated "b" and "c", that run generally parallel to the longitudinal centerline 58. This arrangement of fold lines may allow the central region 76 of the sanitary napkin 10 to assume a trough-like configuration when the sanitary napkin 10 is worn.

Figure 35:
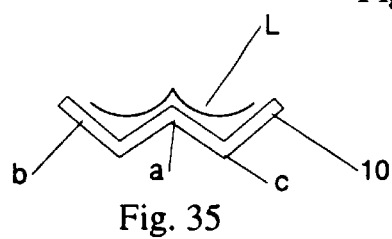

FIG. 35 shows that a sanitary napkin 10 having a stiffened central region 76 with three fold lines, fold line "a" that runs along the longitudinal centerline, and fold lines b and c, that run generally parallel to the longitudinal centerline 58. This arrangement of fold lines may allow the central region 76 of the sanitary napkin 10 to assume a W-shaped configuration when the sanitary napkin 10 is worn.

The configuration of end regions 72 and 74 of the sanitary napkin embodiments depicted in FIGS. 31–35 in use might be similar to those shown in preceding FIGS. 28 and 29.

Looking at some of the elements of the sanitary napkin 10 more specifically, the absorbent core 34 may be any means which is generally compressible, conformable, non-irritating to the wearer's skin and capable of absorbing and containing body exudates. The absorbent core 34 has a first major surface 46, a second major surface 49, a pair of end edges 52 and a pair of side edges 55. The absorbent core 34 may be manufactured in a wide variety of sizes and shapes (e.g., rectangular, hourglass, etc.). A preferred shape of the absorbent core 34 is the dogbone shape shown in FIG. 1. This preferred absorbent core 34 is about 22.0 centimeters long (longitudinal dimension along the longitudinal centerline 58), about 7.0 centimeters wide across its midportion (lateral dimension along the lateral centerline 61) and about 8.0 centimeters wide across its widest portion (lateral dimension).

The absorbent core 34 is symmetrically configured for ease of manufacture and so that no conscious effort is required by the wearer to properly place the napkin 10 in the direction it should be worn. The midportion is configured to basically conform to the wearer's thighs and to the thinner crotch portion of the wearer's panties so as to prevent excessive bunching. The size of the absorbent core 34 may be varied to accommodate wearers ranging in size and also ranging in the expected amount of exudate fluid volume. Preferably, the absorbent core 34 has a wet-tensile strength in the cross-direction of at least about 100.0 grams per centimeter. Wet tensile strength is determinable by ASTM Standard D 829-49.

The absorbent core 34 may be manufactured from a wide variety of liquid absorbent materials commonly used in disposable sanitary napkins, diapers, and other absorbent articles. Examples of suitable absorbent materials include comminuted wood pulp which is generally referred to as airfelt, creped cellulose wadding, modified cross-linked cellulose fibers, absorbent foams, absorbent sponges, synthetic staple fibers, polymeric fibers, hydrogel-forming polymer gelling agents, peat moss, or any equivalent materials or combinations of materials.

A particularly preferred type of absorbent material is polymeric gelling agents. Polymeric gelling agents are those materials which, upon contact with fluids (i.e., liquids) such as water or body fluids, imbibe such fluids and thereby form hydrogels. In this manner, fluid discharged into the absorbent core 34 can be acquired and held by the polymeric gelling agent, thereby providing the articles herein with enhanced absorbent capacity and/or improved fluid retention performance. The polymeric gelling agent which is employed in the absorbent core 34 will generally comprise particles of a substantially water-insoluble, slightly cross-linked, partially neutralized, hydrogel-forming superabsorbent polymer material.

In the embodiment shown in FIG. 2, the absorbent core 34 is a laminate comprised of a layer of superabsorbent polymer material 37 disposed between two air-laid tissues 40 and 43. A suitable laminate is the superabsorbent laminate WATER-LOCK L-535 available from the Grain Processing Corporation of Muscatine, Iowa (WATER-LOCK registered™ by Grain Processing Corporation). Such superabsorbent laminates are disclosed in U.S. Pat. No. 5,009,653 issued to Osborn and the patents incorporated by reference in that patent, the disclosures of which are all incorporated by reference herein, and in U.S. Pat. No. 4,467,012, issued to Pedersen, et al. on Aug. 21, 1984, and U.S. Pat. No. 4,260,443 issued to Lindsay, et al. on Apr. 7, 1981.

The first and second tissue layers 40 and 43 provide containment of the superabsorbent polymer material 37, improve lateral wicking of the absorbed exudates throughout the absorbent core 34 and provide a degree of absorbency.

Within the webs which form the layers of the absorbent core 34, the particles of the polymeric gelling agent should be thoroughly dispersed but may or may not be uniformly distributed. In particular, there may be regions or zones of the core layers which have higher concentrations of gelling agent particles than do other regions or zones of the layers.

In preferred embodiments, the sanitary napkin 10 of the present invention will have a hydrogel-forming polymeric gelling agent distributed throughout at least about 17.0 square centimeters of the napkin, more preferably throughout at least about 50.0 square centimeters of the napkin, and most preferably throughout at least about 100.0 square centimeters of the napkin. Preferably, the hydrogel-forming polymeric gelling agent will be distributed in an amount of from about 0.001 grams per square centimeter to about 0.009 grams per square centimeter, more preferably of from about 0.003 grams per square centimeter to about 0.008 grams per square centimeter, and most preferably from about 0.004 grams per square centimeter to about 0.007 grams per square centimeter. Preferably, the absorbent core 34 will contain from about 5.0% to about 85.0% by weight of hydrogel-forming polymeric gelling agent, more preferably from about 10.0% to about 70.0%, and most preferably from about 15.0% to about 55.0%.

The hydrogel-forming polymer gelling agents can alternatively can comprise non-particulate gelling agents which can be formed into fibrous sheets, foams or films. In these cases, the polymer gelling agent may comprise from about 15% to about 100% by weight of the absorbent core 34, more preferably from about 40% to about 100%, and most preferably from about 60% to about 100%. The basis weight of such non-particulate superabsorbents may be from about 0.002 to about 0.028 grams per square centimeter, more preferably from about 0.003 to about 0.018, and most preferably from about 0.004 to about 0.010. Two suitable and commercially available non-particulate absorbent materials for the absorbent core 34 are a double layer acrylic fibrous material available under the tradename Lanseal F from the Choli Company, LTD., of Higashi, Osaka Japan and a carboxymethylcellulose fibrous material available under the tradename Aqualon C from Hercules, Inc. of Wilmington, Del.

Suitable absorbent cores comprising foams are described in U.S. patent application Ser. Nos. 07/743,839, 07/743,950, 07/743,947, and 07/830,159 (P&G Case Nos. 4451, 4452, 4453, and 4453R) the first, third and fourth applications listed filed in the names of DesMarias, et al., and the second application listed filed in the name of Young, et al. The first three applications were filed on Aug. 12, 1991, and the fourth on Feb. 12, 1992. Additional cores comprising foams are described in European Patent Application 0 293 208 B1. Absorbent cores comprising sponges are described in U.S. Pat. Nos. 3,512,530, 3,954,493 and French Patent 2,203, 827.

Additional suitable absorbent core materials are described in U.S. Pat. Nos. 4,773,903 and 4,865,596 issued to Weisman, et al. on Sep. 27, 1988 and Sep. 12, 1989, respectively. These patents disclose composite absorbent structures comprising webs of entangled blown microfibers, substantially nonabsorbent crimped staple fibers, particles of hydrogel-forming polymeric gelling agents and a hydrophilizing agent.

The total absorbent capacity of the absorbent core 34 should be compatible with the design exudate loading for the intended use of the sanitary napkin 10. Further, the absorbent capacity of the absorbent core 34 may be varied to accommodate wearers ranging in the expected amount of exudate fluid volume. For instance, a different absorbent capacity may be utilized for sanitary napkins intended for daytime use as compared with those intended for nighttime use, or for sanitary napkins intended for use by teenage females as compared with those intended for use by more mature women.

Superimposed over the absorbent core 34 and extending about 3.0 millimeters beyond the edges 52 and 55 of the absorbent core 34 is the wet-laid tissue 31. The wet-laid tissue 31 is liquid permeable. A satisfactory wet-laid tissue 31 has a basis weight of about 15.8 grams per square meter and an air permeability of about 30.5 cubic meters per minute per square meter at a pressure differential of about 12.8 millimeters of water. Preferably, the wet-laid tissue 31 maintains integrity when wetted, in use. The wet-laid tissue 31 preferably has a wet tensile strength in the cross-direction of at least about 15.0 grams per centimeter. Suitable tissues 31 and their manufacture are disclosed in U.S. Pat. No. 3,301,746, which issued to Sanford, et al. on Jan. 31, 1967. In a preferred embodiment, those parts of the wet-laid tissue 31 which extend beyond the edges 52 and 55 of the absorbent core 34 are associated with the barrier sheet 16. The wet-laid tissue 31 may be associated with the barrier sheet 16 by attachment means as are well known in the art such as by spray-gluing or lines or spots of adhesive.

The wet-laid tissue 31 serves a number of purposes. The tissue 31 serves to confine any loose superabsorbent material 37 between the tissue 31 and the barrier sheet 16 thereby preventing the superabsorbent material 37 from coming in contact with the wearer's skin. Also, the tissue 31 improves lateral wicking of the absorbed exudates over the absorbent core 34 thereby providing a more even distribution of the exudates throughout the absorbent core 34. Further, the tissue 31 provides some degree of absorbency and further inhibits exudates which have reached and been absorbed by the absorbent core 34 from rewetting the wearer's skin.

Superimposed over the wet-laid tissue 31 is a liquid permeable wipe acquisition sheet 28. In a preferred embodiment, the wipe acquisition sheet 28 is a nonwoven sheet. In the preferred embodiment shown in FIG. 2, the sheet 28 is a spunlaced 70%/30% rayon/polyester fiber sheet. Spunlaced fabrics of this type are manufactured by E.I. DuPont Nemours & Company of Wilmington, Del., and are made available under the tradename "SONTARA" (SONTARA registered™ by E.I. DuPont Nemours & Company). These fabrics are available in a number of suitable styles, however, Style 8407 in its apertured form, having a basis weight of 0.005 grams per square centimeter and a thickness of about 0.04 millimeters, is preferred.

In a particularly preferred embodiment, the wipe acquisition sheet 28 comprises a spunlace nonwoven web comprised of permanently wettable fibers. Preferably, the acquisition sheet 28 is a 30 g/yard$^2$ (35 g/m$^2$) polyethylene theraphalate (or PET) spunlace nonwoven web. Spunlaced fabrics of this type are manufactured by the Vertec Company of Walpole, Mass. The spunlace nonwoven web is formed so that most of the fibers are oriented in a single direction, and placed in the sanitary napkin so that those fibers extend in the longitudinal direction.

The fibers of this particularly preferred acquisition sheet 28 are made of a PET resin and are coated with a proprietary permanently wettable finish known as CELWET. These fibers are available from the Hoechst Celanese Corporation of Charlotte, N.C. The term "permanently wettable", as used herein, refers to fibers that will sink in less than or equal to about 7 seconds when tested according to the ASTM D 1117-74 Basket Sink Method.

The wipe acquisition sheet 28 extends beyond the edges of the wet-laid tissue 31 where it too is associated with the barrier sheet 16. The wipe acquisition sheet 28 greatly improves lateral wicking of exudates over the absorbent core 34 thereby providing a more even distribution of the exudates throughout the absorbent core 34.

The lateral wicking of the wipe acquisition sheet 28 is important for the following reason. Many bulky prior art sanitary napkins rely on a high degree of vertical absorption at the point where exudates are initially deposited. In other words, because the absorbent cores of these napkins are fairly thick, they can absorb a high degree of exudates throughout their thickness while utilizing only a small degree of their surface area or lateral absorption capability. However, the relatively thin napkins 10 of the present invention have a comparatively small degree of vertical absorption. Therefore, for a relatively large amount of exudates to be absorbed, a wipe acquisition sheet 28 which can laterally disperse the exudates over a large surface area of the absorbent core 34 where the exudates can better and faster be vertically absorbed is highly desirable. Further, the wipe acquisition sheet 28 provides a fairly high degree of initial absorption during the time interval between the time exudates are deposited onto the topsheet 25 and the time they are absorbed by the absorbent core 34. This property will be more specifically described later.

Superimposed over the wipe acquisition sheet 28 is the liquid permeable topsheet 25. The topsheet 25 is compliant, soft feeling, and non-irritating to the wearer's skin. Further, the topsheet 25 is liquid pervious, permitting liquid to readily transfer through its thickness. A suitable topsheet 25 may be manufactured from a wide range of materials such as polymeric materials, formed thermoplastic films, apertured plastic films, porous foams, reticulated foams, natural fibers (e.g., wood or cotton fibers), synthetic fibers (e.g., polyester or polypropylene fibers) or from a combination of natural and synthetic fibers, with apertured formed films being preferred.

Formed films are preferred for the topsheet 25 because they are pervious to liquids and, if properly apertured, have a reduced tendency to allow liquids to pass back through and re-wet the wearer's skin. Thus, the surface of the formed film which is in contact with the body remains dry, thereby reducing body soiling and creating a more comfortable feel for the wearer. Suitable formed films are described in U.S. Pat. No. 3,929,135, which issued to Thompson on Dec. 30, 1975, U.S. Pat. No. 4,324,246, which issued to Mullane, et al. on Apr. 13, 1982, U.S. Pat. No. 4,342,314, which issued to Radel, et al. on Aug. 3, 1982, and U.S. Pat. No. 4,463,045, which issued to Ahr, et al. on Jul. 31, 1984.

In a preferred embodiment of the present invention, the body surface 26 of the topsheet 25 is hydrophilic. The hydrophilic body surface 26 helps liquid to transfer through the topsheet 25 faster than if the body surface 26 was not hydrophilic. This diminishes the likelihood that menstrual fluid will flow off the topsheet 25 rather than being absorbed by the absorbent core 34. In a preferred embodiment, the body surface 26 of the topsheet 25 is made hydrophilic by treating the body surface 26 with a surfactant. It is preferred that the surfactant be substantially evenly and completely distributed throughout the body surface 26 of the topsheet 25. This can be accomplished by any of the common techniques well known to those skilled in the art. For example, the surfactant can be applied to the topsheet 25 by spraying, by padding, or by the use of transfer rolls. Further, the surfactant can be incorporated into the polymeric materials of a formed film topsheet or between or within the fibers of a nonwoven topsheet.

The topsheet 25 may be associated with the wipe acquisition sheet 28 in any suitable manner. Suitable manners include, but are not limited to associating the topsheet 25 with the wipe acquisition sheet 28 with adhesives, such as by spray-gluing or applying lines or spots of adhesives between the topsheet 25 and the wipe acquisition sheet 28.

Alternatively, or additionally, the topsheet 25 may be associated with the wipe acquisition sheet 28 by entangling the fibers of the wipe acquisition sheet 28 with the topsheet 25, by fusing the topsheet 25 to one or more underlying absorbent layers with a plurality of discrete individual fusion bonds, or by any means known in the art. Any of the other components of the sanitary napkin can be attached in similar manners.

Figure 36:
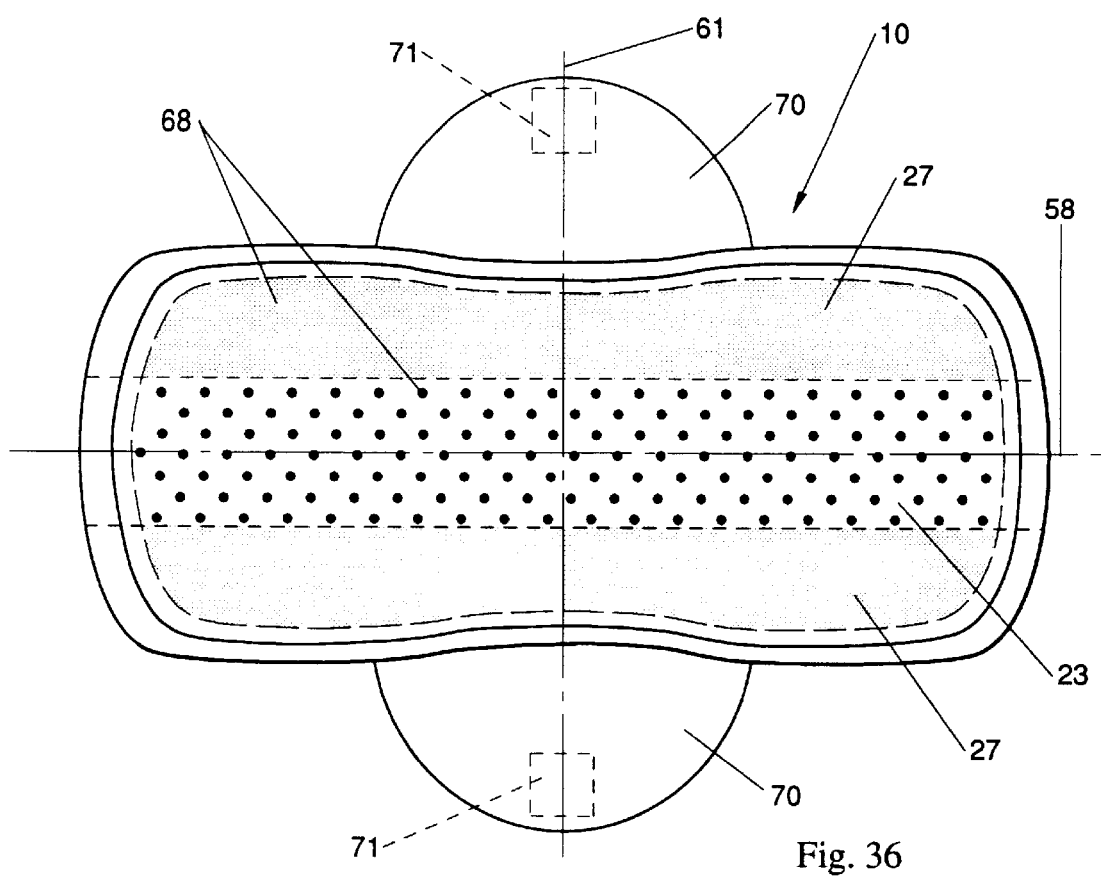
FIG. 36 is a plan view of a sanitary napkin which has a stiffened center formed by folding a wipe acquisition sheet, and a topsheet which is bonded to at least one underlying absorbent layer by a plurality of discrete fusion bonds.
Figure 37:
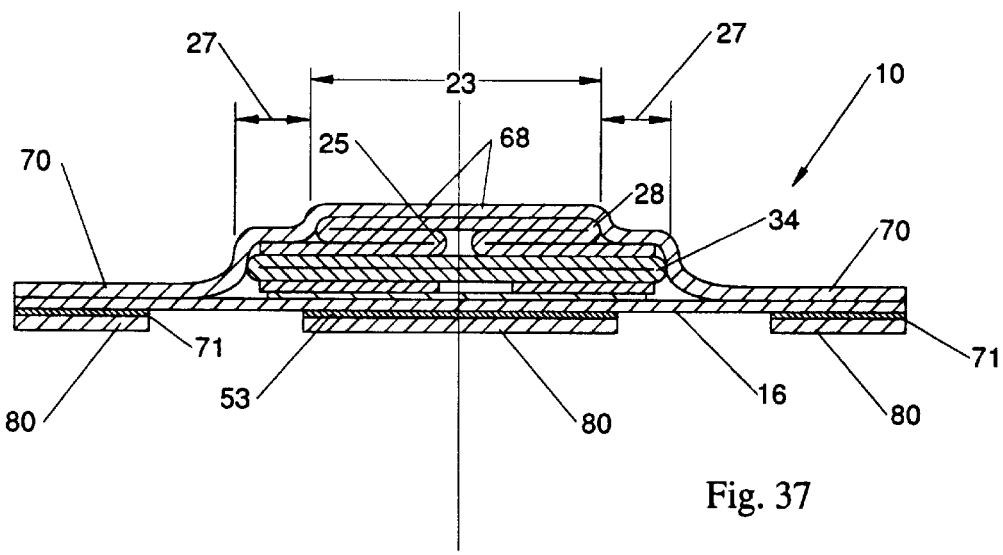
FIG. 37 is a cross-sectional view of the sanitary napkin shown in FIG. 36 taken along line 37–37.

FIGS. 36 and 37 show a preferred type of fusion bonds form bonded areas 68 which provide structures with drainage passageways for liquids to pass through to the underlying absorbent material. These preferred fusion bonds are described in greater detail in U.S. patent application Ser. No. 07/810,774 filed in the names of Cree, et al. on Dec. 17, 1991.

Figure 3:
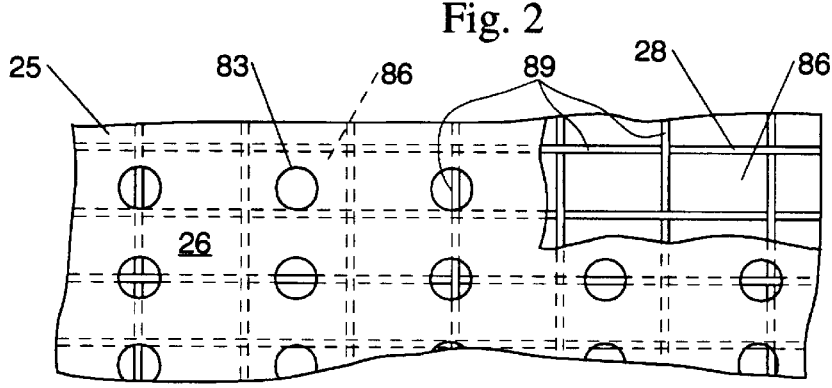
FIG. 3 is a top plan view of a topsheet and wipe acquisition sheet laminate with portions of the topsheet being torn away to show the underlying structure.

The combination of topsheet 25 and wipe acquisition sheet 28 imparts some beneficial properties to the sanitary napkin 10. In particular, the combination of an apertured formed film topsheet 25 superimposed over an apertured nonwoven wipe acquisition sheet 28 is beneficial. A preferred wipe acquisition sheet 28 is the previously described SONTARA 8407. An enlarged depiction of such an arrangement is shown in FIG. 3. Such a combination is even more beneficial when the nonwoven wipe acquisition sheet 28 is formed or positioned such that no fiber bundles 89 of the sheet 28 are beneath some of the apertures 83 of the formed film topsheet 25 (i.e., the apertures in the two sheets 25 and 28 are aligned), while beneath other apertures 83 of the formed film topsheet 25, fiber bundles 89 of the nonwoven sheet 28 are present (i.e., apertures in the two sheets 25 and 28 are not aligned).

Such an arrangement is readily apparent in FIG. 3, wherein the apertures 86 of the nonwoven sheet 28 are larger than the apertures 83 of the formed film topsheet 25. Such an arrangement provides the sanitary napkin 10 at least two beneficial properties: enhanced gush acquisition and enhanced wipe acquisition. Gush acquisition is enhanced in those areas where the apertures 83 of the topsheet 25 are aligned with the apertures 86 of the nonwoven wipe acquisition sheet 28. The aligned apertures 83 and 86 provide a direct route for exudates to flow from the body surface 26 of the topsheet 25 to the central absorbent materials of the napkin 10. Further, the apertures 83 and 86 themselves are able to contain a degree of fluid within their walls or boundaries until such fluid is absorbed. Wipe acquisition, which is the ability to pull liquid exudates from the wearer's skin into the absorbent material of the napkin 10, is enhanced in those areas where fiber bundles 89 of the nonwoven wipe acquisition sheet 28 are aligned such that the fiber bundles 89 are beneath the openings of the apertures 83 of the topsheet 25.

As just mentioned, wipe acquisition is critical in those regions where the topsheet 25 is in contact with exudates on the wearer's skin. In such areas, the sanitary napkin 10 is likely under compressive forces from the wearer's body. When such is the case, the fiber bundles 89 of the nonwoven wipe acquisition sheet 28 beneath the apertures 83 of the topsheet 25 are forced somewhat up into the apertures 83 of the topsheet 25, closer to the wearer's skin. Obviously, the spaces between the fiber bundles 89 and the walls of the apertures 83 or between the fibers of the fiber bundles 89 themselves will be less than the spaces which were between only the walls of the apertures 83. These spaces are capillaries. As is well known in the art, as capillary spaces are decreased, capillary or drawing action is increased. Thus, the capillary action in these apertures 83 where fiber bundles 89 are present is increased and the sanitary napkin 10 is better able to draw exudates from the wearer's skin into these capillaries and eventually into the central absorbent materials of the sanitary napkin 10.

Although all of the apertures 83 of the topsheet 25 are referenced by the numeral "83", for the following teaching purposes, specific reference is directed to the aperture of FIG. 3 specifically labeled and designated "83". The specific aperture 83 referenced is an example in which an aperture 83 of the topsheet 25 is aligned with an aperture 86 of the nonwoven wipe acquisition sheet 28. Theoretically, such an aperture is useful for gush acquisition since exudates have uninterrupted flow from the body surface 26 of the topsheet 25 to the central absorbent material (not shown). Next, attention is directed to the aperture 83 immediately to the right of the specific aperture 83 just referenced. As seen, this aperture 83 is superimposed over a fiber bundle 89 of the nonwoven wipe acquisition sheet 28. Theoretically, exudates that flow into the aperture 83 will enter the capillaries of the fiber bundle 89. The exudates will then either be pulled or absorbed into the central absorbent materials or wicked to intersecting fiber bundles 89, then wicked further to other intersecting fiber bundles 89, and so on, until the exudates are absorbed into a more laterally distant portion of the central absorbent materials. Hence, a large portion of the total absorbent capacity of the absorbent materials can be utilized.

The barrier means 16 is adjacent the second major surface 22 of the absorbent means 13. In a preferred embodiment, the absorbent means 13 may be affixed over the second major surface 22 of the absorbent means 13 to the barrier means 16. Any of the techniques described above for affixing the topsheet 25 to the wipe acquisition sheet 28 may be used for this purpose. The barrier means 16 generally defines the garment surface 17 of the sanitary napkin 10.

The barrier means 16 may be any means which is impervious to liquids and which prevents exudates absorbed and contained in the absorbent means 13 from soiling articles, such as panties, which come in contact with the garment surface 17 of the sanitary napkin 10. In the preferred embodiment of the sanitary napkin 10 illustrated in FIGS. 1 and 2, the barrier means 16 is a barrier sheet manufactured from a thin plastic film. Other flexible liquid impervious materials may also be used. Preferably, the barrier sheet 16 is a polyethylene film having a thickness of from about 0.012 millimeter to about 0.051 millimeter. As used herein, the term "flexible" refers to materials which are compliant and which will readily conform to the general shape and contours of the human body.

A suitable polyethylene film is manufactured by Monsanto Chemical Corporation and marketed in the trade as Film No. 8020. The barrier sheet 16 is preferably embossed and/or matte finished to provide a more clothlike appearance. Further, the barrier sheet 16 may permit vapors to escape from the absorbent means 13 while still preventing exudates from passing through the barrier sheet 16.

Preferably, the topsheet 25 and the barrier sheet 16 have length and width dimensions generally larger than the absorbent core 34 so that they extend beyond the edges 52 and 55 of the absorbent core 34 where they are associated together in a suitable manner. As used herein, the term "associated" encompasses configurations whereby a first member is directly joined to a second member and configurations whereby a first member is indirectly joined to a second member by affixing the first member to intermediate members which in turn are affixed to the second member. The extension of the topsheet 25 and/or the barrier sheet 16 beyond the core end edges 52 and the core side edges 55 of the absorbent core 34 form the end edges 11 and the side edges 12, respectively, of the sanitary napkin 10. In one preferred embodiment, the barrier sheet 16 and the topsheet 25 have an elliptical shape and extend beyond the absorbent core 34 a distance of at least about 1.0 centimeter where they are joined directly to each other by attachment means as are well known in the art. The attachment means may include, but are not limited to adhesives, heat, and/or on ultrasonic bonds.

The sanitary napkin 10 is described as being generally flexible. The term "generally flexible", as used herein, means that the sanitary napkin 10 can have a relatively inflexible longitudinal central region 23, or central region 76, provided it has relatively flexible respective longitudinal side regions 27, or end regions 72 and 74, so that the sanitary napkin 10 is comfortable for the wearer.

The flexibility of the various regions of the sanitary napkin is expressed in terms of flexure-resistance. The flexibility is measured according to the Circular Bend Procedure (described in greater detail below). The longitudinal central region 23 and the central region 76 preferably have flexure-resistances of less than or equal to about 1,000 grams, more preferably less than or equal to about 700 grams, even more preferably less than or equal to about 500 grams, and most preferably less than or equal to about 400 grams.

The longitudinal side regions 27 and the end regions 72 and 74 preferably have flexure resistances of less than or equal to about 700.0 grams, more preferably less than or equal to about 600 grams, more preferably less than or equal to about 500 grams, more preferably less than or equal to about 400 grams, and most preferably less than about 250 grams. The flexure-resistance of the longitudinal side regions 27 or end regions 72 and 74 may also be any of those figures specified for the sanitary napkin described in U.S. Pat. No. 5,009,653 issued to Osborn.

The flexure-resistance of the longitudinal central region 23 or central region 76 is always greater than the flexure-resistance of the respective longitudinal side regions 27 or end regions 72 and 74.) The relative difference in flexibility of the various regions should preferably be such that the flexure-resistance of the longitudinal central region 23 or central region 76 is 25% greater, more preferably 50% greater than that of the respective longitudinal side regions 27 or end regions 72 and 74.

The flexure-resistance of the different regions of the sanitary napkin are measured by peak bending stiffness. Peak bending stiffness is determined by a test which is modeled after the ASTM D 4032-82 Circular Bend Procedure. The ASTM procedure is modified for use herein. The Circular Bend Procedure as modified and used for the purposes of the present invention is hereinafter simply referred to as the "Circular Bend Procedure". One version of the Circular Bend Procedure is described in U.S. Pat. No. 5,009,653 issued to Osborn. The Circular Bend Procedure is a simultaneous multi-directional deformation of a material in which one face of a specimen becomes concave and the other face becomes convex. The Circular Bend Procedure gives a force value related to flexure-resistance, simultaneously averaging stiffness in all directions.

In the case of the present invention when carrying out the Circular Bend Procedure, rather than using one set of samples taken from the significant absorbent portions of the sanitary napkin as described in U.S. Pat. No. 5,009,653, separate samples of the sanitary napkins are taken from longitudinal central region 23 (or central region 76) and from the longitudinal side regions 27 (or end regions 72 and 74). The samples are tested and averaged separately so a flexure-resistance value is obtained for the longitudinal central region 23, and a separate value is obtained for the longitudinal side regions 27 (or end regions 72 and 74).

Apparatus

The apparatus necessary for the CIRCULAR BEND PROCEDURE is a modified Circular Bend Stiffness Tester, having the following parts:

A smooth-polished steel plate platform which is 102.0× 102.0×6.35 millimeters having an 18.75 millimeter diameter orifice. The lap edge of the orifice should be at a 45 degree angle to a depth of 4.75 millimeters.

A plunger having an overall length of 72.2 millimeters, a diameter of 6.25 millimeters, a ball nose having a radius of 2.97 millimeters and a needle-point extending 0.88 millimeter therefrom having a 0.33 millimeter base diameter and a point having a radius of less than 0.5 millimeter, the plunger being mounted concentric with the orifice and having equal clearance on all sides. Note that the needle-point is merely to prevent lateral movement of the test specimen during testing. Therefore, if the needle-point significantly adversely affects the test specimen (for example, punctures an inflatable structure), than the needle-point should not be used. The bottom of the plunger should be set well above the top of the orifice plate. From this position, the downward stroke of the ball nose is to the exact bottom of the plate orifice.

A force-measurement gauge and more specifically an Instron inverted compression load cell. The load cell has a load range of from about 0.0 to about 2000.0 grams.

An actuator, and more specifically the Instron Model No. 1122 having an inverted compression load cell. The Instron 1122 is made by the Instron Engineering Corporation, Canton, Mass.

Number and Preparation of Specimens

In order to perform the procedure for this test, as explained below, five representative sanitary napkins are necessary. From one of the five napkins to be tested, some number "Y" of 37.5×37.5 millimeter test specimens are cut. At least one specimen is cut from the center (specifically, the longitudinal central region or the central region) of the sanitary napkin, and at least one specimen is cut from the longitudinal side regions or end regions of the sanitary napkin. If due to the plan view shape of the region to be tested, it is not possible to cut a square 37.5×37.5 mm. specimen, any other 1,400 square millimeter size specimen may be used, provided the specimen adequately covers the orifice in the test platform to properly carry out the test. Specimens should not be taken which contain score or fold lines.

Specimens having portions in which a topsheet is joined directly to a barrier sheet or which are a laminate of a topsheet, two or less tissue sheets and a barrier sheet, should also not be tested. The reason that these specimens are not tested is due to the realization that prior art napkins exist in which a topsheet is joined to a barrier sheet beyond the edges of an absorbent core in the periphery of the napkin, such portions of which are highly flexible. The present invention is more concerned with the flexibility of the significant absorbent portions of the sanitary napkin. If any of the significant absorbent portions of the sanitary napkin meet the parameters set forth in the appended claims for the particular regions, then the sanitary napkin falls within the scope of the appended claims. A number of different specimens should be tested from each sanitary napkin. In particular, the structurally least flexible portions in the center of the sanitary napkin should be tested as the longitudinal center region and the central region. The most flexible portions of the sanitary napkin should be tested when samples of the longitudinal side regions and end regions of the napkin are measured.

The test specimens should not be folded, bent, or compressed by the test person, and the handling of specimens must be kept to a minimum and to the edges to avoid affecting flexural-resistance properties. From the four remaining sanitary napkins, an equal number "Y" of specimens, identical to the specimens cut from the first napkin, are cut. Thus, the test person should have "Y" number of sets of five identical specimens.

Procedure

The procedure for the CIRCULAR BEND PROCEDURE is as follows. The specimens are conditioned by leaving them in a room which is 21±1° C. and 50±2% relative humidity for a period of two hours. The test plate is leveled. The plunger speed is set at 50.0 centimeters per minute per full stroke length. A specimen is centered on the orifice platform below the plunger such that the body surface 26 of the specimen is facing the plunger and the garment surface 17 of the specimen is facing the platform with the release paper removed from any adhesive on the garment surface of the specimen and the adhesive sprinkled with corn starch to eliminate the adhesive tack. The indicator zero is checked and adjusted, if necessary. The plunger is actuated. Touching the specimen during the testing should be avoided. The maximum force reading to the nearest gram is recorded. The above steps are repeated until all five of the identical specimens have been tested.

Calculations

The peak bending stiffness for each specimen is the maximum force reading for that specimen. Each set of five identical specimens is tested and the five values received for that set are averaged. Thus, the test person now has an average value for each of the "Y" identical sets of specimens tested. If any of the significant absorbent portions of the sanitary napkin have a longitudinal central region and longitudinal side regions or a central region and end regions with average for each identical specimen with the requisite flexure-resistances, then the napkin satisfies the parameters of this test.

The sanitary napkin 10 of the present invention has a liquid capacity great enough to absorb medium to high menstrual flows. Two capacities, which, depending on the size of the sanitary napkin may be the same, are determinable: test capacity and total capacity. Preferably, the napkin 10 of the present invention has a test capacity of at least about 8.0 grams, more preferably of at least about 15.0 grams, and most preferably of at least about 18.0 grams. Preferably, the napkin 10 of the present invention has a total capacity of at least about 20.0 grams, more preferably of at least about 30.0 grams, and most preferably of at least about 40.0 grams.

The test and total capacities of a sanitary napkin are determined as follows. Any panty adhesive release paper is removed from the napkin to be tested. To determine test capacity, a sample is obtained from a 4.75×14.0 centimeters portion, or any other configuration having 66.5 square centimeters, of the sanitary napkin. The sample is cut from the portion of the sanitary napkin which would be centered under the vaginal orifice when the sanitary napkin is worn. Total capacity is determined using a sample comprising the entire napkin minus any release paper.

The sample is weighed to the nearest 0.1 gram. The sample is then submerged in a beaker of sterile saline (obtainable from the Baxter Travenol Company of Deerfield, Ill.), such that the sample is totally submerged and is not bent or otherwise twisted or folded. The sample is submerged for 10 minutes. The sample is removed from the saline and suspended for two minutes in a vertical position to allow the saline to drain out of the sample. The sample is then placed body facing surface down onto an absorbent blotter, such as the filter paper #631 available from the Filtration Science Corp., Eaton-Dikeman Division of Mount Holly Springs, Pa. A uniform 17.6 grams per square centimeter load is placed over the sample to squeeze excess fluid out. The absorbent blotter is replaced every 30 seconds until the amount of fluid transferred to the absorbent blotter is less than 0.5 grams in a 30 second period. Next, the sample is weighed to the nearest 0.1 gram and the dry weight of the sample is subtracted. The difference in grams is the test or total capacity of the sample, whichever the case may be.

The sanitary napkin 10 should preferably be scaled to the width of the crotch of the underwear of the wearer. A sanitary napkin 10 having a central absorbent width 63 which registers the absorbent 13 with the edges of the underwear crotch is particularly preferred. For relatively narrower underwear crotches, having a width of about 3.7 to about 6.4 centimeters, a sanitary napkin having a central absorbent width 63 of about 3.7 to about 6.4 centimeters works well. The term "central absorbent width" and a method of measuring the same is described in U.S. Pat. No. 5,009,653.

The total width of the napkin 10 is scaled to the central absorbent width 63, and should be about 0.6 to about 1.0 centimeters greater than the central absorbent width 63, due to the additional margin necessary to join the edges of the topsheet 25 and barrier sheet 16 together. Generally about 0.3 to about 0.5 centimeters are necessary at each edge of the napkin 10 to join the topsheet 25 to the barrier sheet 16. Thus, a napkin having a central absorbent width 63 of about 3.7 to about 6.4 centimeters will have a total width ranging from about 4.3 to 4.7 centimeters to about 7.0 to 7.4 centimeters.

The sanitary napkin 10 of one embodiment of the present invention intended for underwear having a relatively greater crotch width should have a central absorbent width 63 of at least about 6.5 centimeters, more preferably of at least about 7.0 centimeters, more preferably of at least about 7.75 centimeters, and most preferably of at least about 9.0 centimeters.

As the central absorbent width 63 of the sanitary napkin 10 diminishes, the total capacity, as determined by the aforementioned Test Procedure, will proportionally diminish, unless the sanitary napkin 10 is lengthened in the longitudinal direction. Because a pad which is excessively lengthened may not be comfortable to wear, it is acceptable, for a pad having a central absorbent width 63 of about 6.2 centimeters or less to have a reduced total capacity. For such an arrangement a sanitary napkin 10 having a total capacity of about 14 grams has been found to work well.

The central absorbent width 63 of the sanitary napkin 10 of the present invention is believed important for the following reason. The sanitary napkin 10 of the present invention relies more on the lateral distribution of exudates over or through a relatively large surface area of the absorbent core 34 than on a high degree of vertical absorption common to many prior art sanitary napkins. Therefore, because exudates which are distributed onto the topsheet 25 may not be quickly absorbed before they migrate across the topsheet 25, it is important to contain such exudates pending absorption.

The specified central absorbent width 63 of the sanitary napkin 10 of the present invention has been determined based on the width of a flexible napkin which will cup around the labia in the region of the vaginal orifice such that at least the edges of the absorbent material are positioned in the uppermost part of the wearer's legs at the crotch. Thus, the sanitary napkin 10 and the absorbent material may be cupped shaped in the surrounding regions of the vaginal orifice and exudates deposited thereon will be contained until absorbed.

The sanitary napkins 10 of the present invention of the present invention are relatively thin. It is preferred to keep the sanitary napkins 10 of the present invention relatively thin so that the sanitary napkins 10 of the present invention will be unobtrusive and the user will have a low awareness of the sanitary napkin while it is being worn. The sanitary napkin 10 shown in FIGS. 1 and 2 may have a caliper of about 1.9 millimeters. The caliper of a sanitary napkin 10, or various regions thereof, is determined by the following test.

A comparator gauge, and specifically the Ames, Model 130 with dial indicator Model 482, available from the B.C. Ames, Company of Waltham, Mass. is needed. The comparator gauge should have a circular comparator foot made of aluminum and having a weight of 10.0 grams and a contact surface of 5.16 square centimeters. The comparator gauge is zeroed. An 80.0 grams stainless steel weight is placed on the spindle extending above the comparator dial. The comparator foot is raised and the napkin, with any panty adhesive release paper being removed and the adhesive is sprinkled with corn starch, and napkin is placed garment surface down on the base plate. The napkin is positioned on the base plate so that when the foot is lowered it is in the region of the napkin for which the measurement is desired. Try to smooth out or avoid any wrinkles in the napkin. Gently lower the foot onto the napkin. Determine the napkin caliper by reading the comparator dial 30 seconds after the foot comes in contact with the napkin.

At least one measurement is taken in the longitudinal central region or central region of the sanitary napkin along the longitudinal centerline 58, and at least one measurement is taken in the respective longitudinal side regions or end regions of the sanitary napkin.

Preferably, the sanitary napkins 10 of the present invention have longitudinal side regions 23 or end regions 72 and 74 with a caliper of less than about 2.6 millimeters, more preferably less than about 2.2 millimeters, and most preferably less than about 2.0 millimeters. The caliper of the longitudinal side regions 23 or end regions 72 and 74 of the sanitary napkin of the present invention may be increased, in less preferred embodiments, proportional to an increase in the flexure-resistance. If the flexure-resistance is increased to greater than about 400 grams, or even greater than about 500 grams, the caliper may be increased to as much as about 4.0 to about 5.0 millimeters, but preferably is not greater than about 3.0 millimeters.

Figure 4:
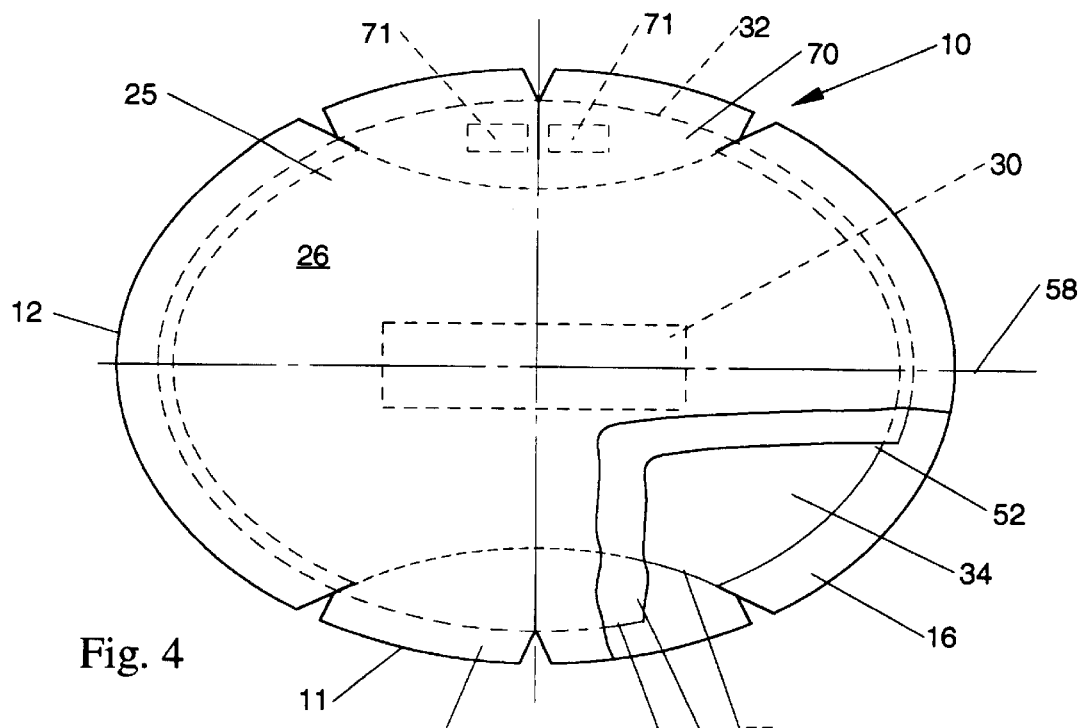
FIG. 4 is a top plan view of an alternative sanitary napkin with portions being torn away to show the underlying structure.

An alternative embodiment of a sanitary napkin 10 of the present invention is shown in FIG. 4. In this embodiment, the sanitary napkin 10 has two flaps 70 each of which are adjacent to and extend laterally from a side edge 55 of the absorbent core 34. The flaps 70 are configured to drape over the edges of the wearer's panties in the crotch region so that the flaps 70 are disposed between the edges of the wearer's panties and the wearer's thighs.

The flaps 70 serve at least two purposes. First, the flaps 70 help serve to prevent soiling of the wearer's body and panties by menstrual fluid. Second, the flaps 70 are preferably provided with attachment means 71 on their garment surface 17 so that the flaps 70 can be folded back under the panty and attached to the garment facing side of the panty. In this way, the flaps 70 serve to keep the napkin 10 properly positioned in the panty. A preferred attachment means 71 is a pressure-sensitive adhesive, as is well known in the art. Alternatively, the flaps 70 may be attached to each other on the underside of the panty by the attachment means 71 without being affixed to the panty.

In the preferred embodiment shown, the flaps 70 are comprised of topsheet 25, tissue 31, and barrier sheet 16. Further, in the embodiment shown, the flaps 70 are unitary with the laminae of the napkin 10. In other words, the topsheet 25, tissue 31 and barrier sheet 16 simply extend laterally beyond the core 34 to form the flaps 70. However, the flaps 70 need not be unitary with the napkin 10 but can be separate elements which are affixed to the napkin 10. Further, the flaps 70 can be comprised of a single substrate or other laminae configurations. It is recommended, however, that the flaps 70 have a liquid impervious barrier sheet 16. The barrier sheet 16 prevents exudates which reach the flaps 70 from soiling the edges of the wearer's panties.

Further, it is preferable that the flaps 70 be provided with an absorbent layer, at least to a point beyond the edges of the wearer's panties. Theoretically, only a relatively small amount of menses should reach the flaps 70, therefore, only a relatively small amount of absorbent material is desirable in the flaps 70. However, at least some absorbent material is recommended in order to prevent any exudates that reach the flaps 70 from being able to flow further to unprotected areas. The absorbent material may be a tissue, such as the tissue 31, or an extension of the absorbent core 34, such as the WATER-LOCK L-535. However, the absorbent material in the flaps 70 should be relatively highly flexible.

For illustration purposes, the central absorbent width 63 of the napkin 10 shown in FIG. 4 would extend laterally from the outer edge 32 of the tissue 31 in the one flap 70 to the outer edge 32 of the tissue 31 in the other flap 70.

Figure 5:
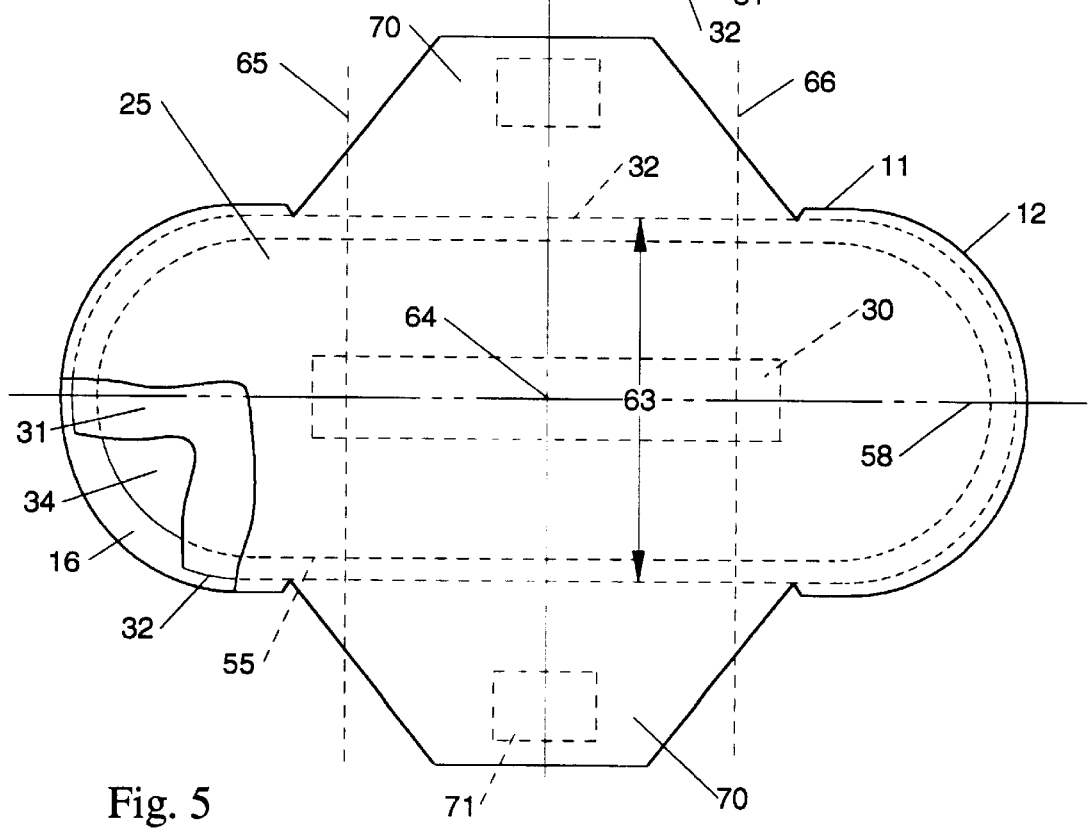
FIG. 5 is a top plan view of another alternative sanitary napkin with portions being torn away to show the underlying structure.

Another alternative embodiment of a sanitary napkin 10 of the present invention is shown in FIG. 5. Like the napkin 10 shown in FIG. 4, this napkin 10 also has flaps 70, only of a different configuration. In this embodiment, the flaps 70 are comprised only of the topsheet 25 and the barrier sheet 55.

For illustration purposes, the central absorbent width 63 of the napkin 10 shown in FIG. 5 would extend laterally from one outer edge 32 of the tissue 31 to the other outer edge 32 of the tissue 31.

A number of sanitary napkins having flaps suitable or adaptable for use with the sanitary napkins 10 of the present invention are known. Such flaps are disclosed in U.S. Pat. No. 4,687,478, entitled "Shaped Sanitary Napkin With Flaps", which issued to Van Tilburg on Aug. 18, 1987, U.S. Pat. No. 4,608,047, entitled "Sanitary Napkin Attachment Means", which issued to Mattingly on Aug. 26, 1986, U.S. Pat. No. 4,589,876, entitled "Sanitary Napkin", which issued to Van Tilburg on May 20, 1986, and U.S. Pat. No. 4,285,343, entitled "Sanitary Napkin", which issued to McNair on Aug. 25, 1981.

While a preferred sanitary napkin embodiment of the present invention has been described, numerous other sanitary napkin embodiments are disclosed in the literature. These could also be provided with the stiffened center of the present invention. several such sanitary napkins are disclosed in U.S. Pat. No. 4,950,264 issued to Osborn on Aug. 21, 1990, U.S. Pat. No. 5,007,906 entitled "Decoupled Sanitary Napkin" issued to Osborn, et al. on Apr. 16, 1991, U.S. Pat. No. 5,009,653 issued to Osborn on Apr. 23, 1991, U.S. Pat. No. 4,917,697 issued to Osborn, et al. on Apr. 17, 1990, and the aforementioned European Patent Application Publication Nos. 0 335 252 and 0 335 253 published in the name of Buell on Oct. 4, 1989 and European Patent Application Publication No. 0 471 114 A2 on Feb. 19, 1992, and in U.S. patent application Ser. No. 07/605,583 entitled, "Sanitary Napkin Having Components Capable of Separation in Use" filed in the name of Visscher, et al. on Oct. 29, 1990, U.S. patent application Ser. No. 07/630,451 entitled "Sanitary Napkin Having Transversely Segmented Core" filed in the name of Osborn, et al. on Dec. 19, 1990, U.S. patent application Ser. No. 07/707,233 entitled "Sanitary Napkin Having Laterally Extensible Means for Attachment to the Undergarment of the Wearer", filed May 21, 1991 in the name of Osborn, et al., and in the Capillary Channel Fiber patent applications described below.

The sanitary napkin of the present invention can, for example, be provided with a flexure resistant deformation element similar to those described in European Patent Application Publication Nos. 0 335 252 and 0 335 253. The flexure resistant deformation element could be used to assist the sanitary napkin in assuming certain configurations when it is worn. For instance, such an element could be used to make regions of the sanitary napkin predisposed to bend upward or downward when the napkin is worn.

The flexure resistant deformation element could be used in many of the embodiments described herein. A deformation element is believed to be particularly well-suited for use with embodiments having a stiffened central region such as those shown in FIGS. 27 and 30. For instance, the stiffened longitudinal central region 23 shown in FIG. 27 and the central region 76 shown in FIG. 30 could comprise a deformation element.

The deformation element could be used in addition to the stiffening material. Alternatively, it could replace the stiffening material. In still other alternatives, the deformation element could replace one of the other components of the sanitary napkin. For example, it could be used as a backsheet. In all such embodiments, the various regions of the sanitary napkin must have the dimensions and flexibilities specified herein.

The deformation element could comprise a foam insert piece. The deformation element could be placed in any suitable place in the sanitary napkin 10. For instance, the deformation element could be placed on top of the absorbent core 34. Alternatively, it could be located underneath the absorbent core 34. In still other alternative embodiments, it could be located on the backsheet 16.

The deformation element could be liquid pervious or liquid impervious. It may also be absorbent. If the deformation element is placed on top of the core, it could be pervious or impervious. In such a case, it is impervious, it could be used to serve a liquid-directing function. However, in cases where the deformation element is placed on top of the core, it is preferably pervious. In embodiments having a deformation element underneath the core, the deformation element is typically liquid impervious.

The disclosures of all patents, patent applications (and any patents which issue thereon, as well as any corresponding published foreign patent applications), and publications mentioned throughout this patent application are hereby incorporated by reference herein. It is expressly not admitted, however, that any of the documents incorporated by reference herein teach or disclose the present invention. It is also expressly not admitted that any of the commercially available materials or products described herein teach or disclose the present invention.

In a particularly preferred alternative embodiment, the sanitary napkin 10 is comprised of components that are extensible (preferably, capable of stretching), particularly in the longitudinal direction when the sanitary napkin is worn. Preferably, the sanitary napkin 10 is capable of elongating between about 15% and about 40% of its unstretched length. This extensibility provides better in-use fit, comfort, and decreased staining when the sanitary napkin is affixed to the wearer's undergarments.

Figure 38:
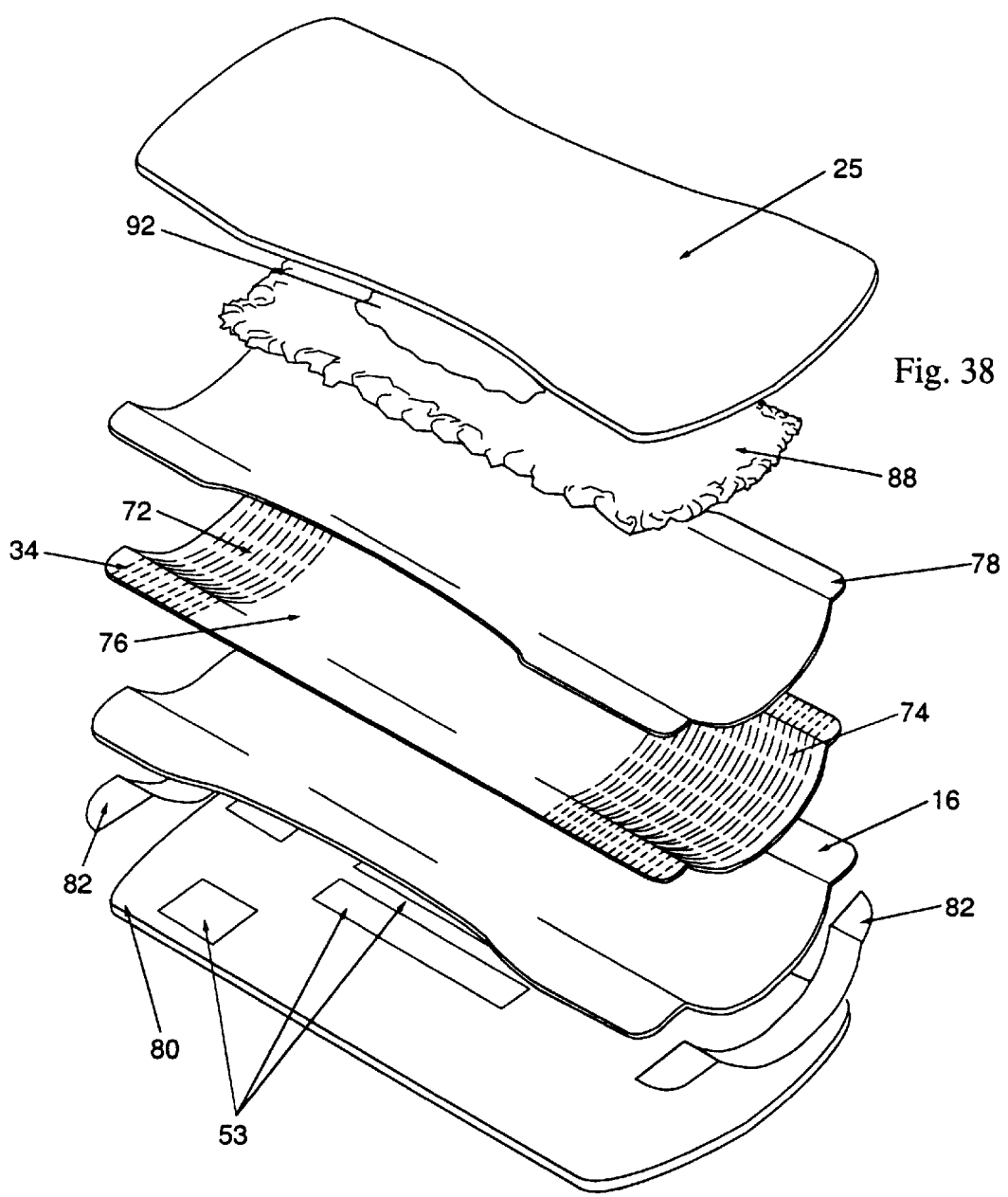
FIG. 38 is an exploded perspective view showing the assembly of a sanitary napkin according to the present invention which contains extensible components.

In one preferred embodiment of the present invention shown in the exploded perspective view of FIG. 38, the topsheet 25 is made in accordance with U.S. Pat. No. 4,463,045 and ring rolled to provide it with a degree of longitudinal extensibility. The fold lines in the corrugations of a ring rolled topsheet 25 should run in the transverse direction so the topsheet 25 is longitudinally extensible.

Such a topsheet 25 is described in the following patent applications which were filed on Jun. 23, 1991: U.S. patent application Ser. No. 07/734,404 filed in the names of Thompson, et al.; U.S. patent application Ser. No. 07/734, 392 filed in the names of Thompson, et al.; and, U.S. patent application Ser. No. 07/734,405 filed in the names of Buenger, et al. These patent applications may be referred to collectively as the "Capillary Channel Fiber" patent applications.

Suitable processes for ring rolling or "pre-corrugating" are described in U.S. Pat. No. 4,107,364 issued to Sisson on Aug. 15, 1978, U.S. Pat. No. 4,834,741 issued to Sabee on May 30, 1989 and in co-pending, commonly assigned U.S. patent application Ser. No. 07/662,536 filed by Gerald M. Weber et al. on Feb. 28, 1991, U.S. patent application Ser. No. 07/662,537 filed by Kenneth B. Buell et al. on Feb. 28, 1991, and U.S. patent application Ser. No. 07/662,543 filed by Gerald M. Weber et al. on Feb. 28, 1991.

FIG. 38 shows that in a particularly preferred embodiment, the absorbent core 34 is a laminate as described above which is slitted or partially slitted for longitudinal extensibility. FIG. 38 shows an absorbent core 34 that is slit at the end regions 72 and 74, but not at the central region 76. Other types of slit absorbent materials are described in European Patent Application Publication Number 0 293 208 B1 published by Lion Corporation on Jul. 24, 1991.

A particularly preferred extensible backsheet 16 is an extended adhesive film known as Formula #198-388 manufactured by the Findley Adhesives Company of Wauwatosa, Wis.

The sanitary napkin 10 shown in FIG. 38 also preferably comprises a layer of capillary channel fibers 88. The layer of capillary channel fibers are gathered at the center into a tuft 92. The sanitary napkin 10 further comprises a creped BOUNTY™ paper towel layer 78 and polyethylene end gaurds 82.

The longitudinal and end edges 11 and 12 of the sanitary napkin 10 are preferably sealed to prevent the wicking and expulsion of liquid or liquid-containing superabsorbent material from the napkin when it is extended. Alternatively, the edges of the absorbent core 34, such as side edges 55, may be sealed rather than sealing the edges of the entire sanitary napkin. The edges of the core 34 may, for example, be wrapped or covered by a tissue layer. In other alternative embodiments, the edges of the tissue may be folded, or otherwise manipulated to prevent the wicking and expulsion of liquid or liquid-containing absorbent material particles 37 from the core 34.

FIG. 38 shows one preferred adhesive configuration for use on this extensible sanitary napkin embodiment. The adhesive configuration shown comprises six ¾"×¾" (about 2 cm.×2 cm.) square pieces of adhesive 53 and two ¾"×2.5" (about 2 cm.×6.4 cm.) longitudinally-oriented rectangular pieces 53. One rectangular piece is positioned on each side of the longitudinal centerline 58. The square pieces are placed in the end regions 72 and 74 of the sanitary napkin 10. The square pieces are placed so that in each end region, one piece is in each corner 14, and one is disposed along the longitudinal centerline 58.

The adhesive patches 53 can be extensible, inextensible, or some patches can be extensible and some inextensible. In another preferred embodiment, the adhesive patches 53 comprise extensible adhesive which are in the configurations shown in FIGS. 22 or 23.

The adhesive patches 53 can each be covered with a separate release liner or cover strip 80. However, the patches are preferably covered with a single release sheet for ease of manufacture and so that the consumer does not have to dispose of several small individual cover strips 80. Any commercially available release liner can be used. In one preferred embodiment, the release liner could be replaced by a wrapper that provides both an individually packaged sanitary napkin and a container for disposing the sanitary napkin after use, such as is described in U.S. Pat. No. 4,556,146 issued to Swanson, et al. on Dec. 3, 1985.

The following Example further illustrates possible constructions of this preferred extensible embodiment of the invention, but is not intended to limit the sanitary napkins encompassed herein.

EXAMPLE I

A sanitary napkin article is hand-made using the following components. Reference is made to FIG. 38 for the assembly of the product.

Figure 39:
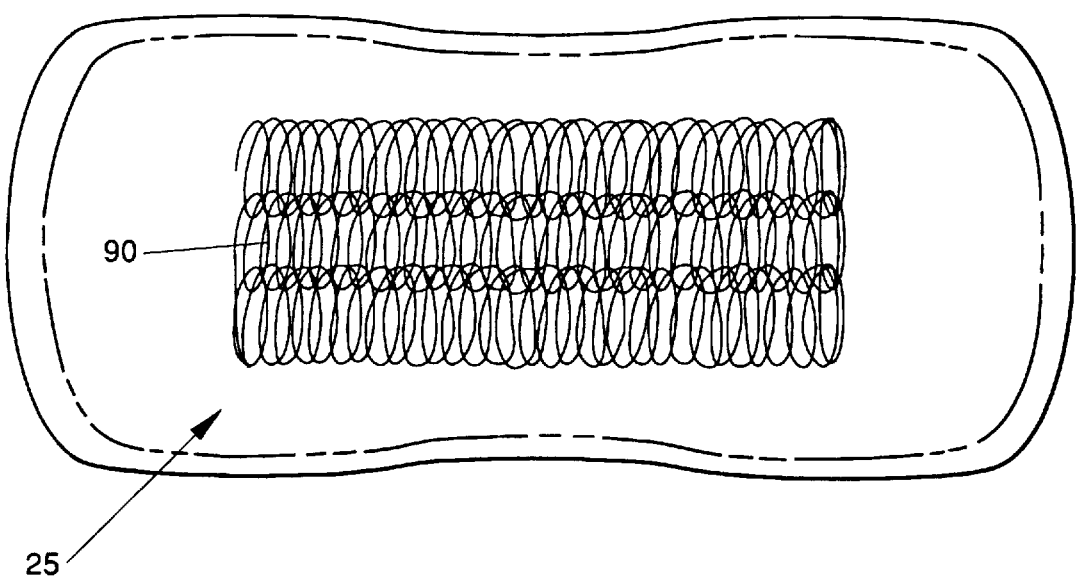
FIG. 39 is a plan view showing a preferred glue pattern applied to the underside of the topsheet of the napkin shown in FIG. 38.

In the making procedure, the ring rolled topsheet is cut to the desired size, a template (2"×7" opening) is placed on the back side of the topsheet and sprayed with a hot melt adhesive known as Findley 4031 adhesive available from Findley Adhesives, Inc. The adhesive is applied in a spiral pattern (see FIG. 39).

A layer of capillary channel fibers which serves as a stiffening material is hand-pressed in the center of the glued area with the fibers running substantially parallel to the long axis of the topsheet. The capillary channel fibers are preferably pressed into the center of the glued area so that they at least partially protrude into the apertures of the topsheet. The provides a Pre-Assembly of the topsheet and capillary channel fibers.

The capillary channel fibers are preferably substantially curled. Suitable capillary channel fibers are those designated SW173 available from the Eastman Chemical Company. The SW173 fibers comprise a carded staple sliver which has been stuffer box crimped to 7.8 crimps per inch and have an H-shaped cross-section with a channel width of 38 microns and a channel depth of 19 microns. The capillary channel fibers are preferably 7 in. long; 0.75 g. fibers are used.

A Findley extended adhesive backsheet (in the form of a polyethylene backsheet with adhesive coating and release paper) is placed on a flat surface. Place the slitted superabsorbent (or absorbent gelling material, or "AGM") laminate core on the Findley backsheet. A creped BOUNTY tissue shaped similarly to the topsheet 25 shown in FIG. 38 is centered over the laminate core. Center the topsheet/capillary channel fiber Pre-Assembly over the creped tissue. Secure the Pre-Assembly and smooth at edges. Roll the edges to seal the edges with the adhesive on the backsheet. Peel the release paper from the back of the pad. Tear and remove in 2 or 3 pieces, then place the polyethylene end gaurd strips on the ends of the article. Place the strips of panty fastening adhesive (PFA) on the pad. Spray the topsheet with 0.01 g. of PEGOSPERSE surfactant available from Lonza, Inc., Williamsport, Pa.

The specifications of the finished product are as follows.

| Parameter | Specifications |
| --- | --- |
| Pad weight (g) | 8.50 ± 0.18 |
| Core weight (g) laminate | 2.54 ± 0.09 |
| Pad length (mm) | 232 ± 4 |
| Core length (mm) laminate | 201 ± 1 |
| Pad width at center (mm) | 85 ± 1 |
| Core width at center (mm) | 65 ± 1 |
| Pad caliper (in. at 0.13 psi) | 0.211 ± 0.005 |
| Core caliper (in. at 0.13 psi) | 0.074 ± 0.003 |

-continued

| Components | Specifications |
|---|---|
| Polyethylene formed-film topsheet (ring rolled; per U.S. Pat. No. 4,463,045) | 9" × 5" |
| Capillary channel fibers SW173 (Eastman) | 0.75 g; 7" length |
| Findley extended adhesive backsheet (Formula #198-338) | ~9" × 5" |
| Creped BOUNTY paper towel | Shaped* |
| PFA (panty fastening adhesive) | Six ¾" × ¾" pieces and two ¾" × 2.5" pieces |
| Release paper | As needed |
| PEGOSPERSE | 0.01 g |
| White poly for ends | 4" × ¾" |
| AGM slit core non-slit center; total core weight 2.5 g; contains 0.7 g AGM | 65 mm × 193 mm with 2 ¾" non-slit center |
| Findley 4031 (adhesive) | 0.05 g |

*The shape is designed to provide anatomical fit.

In one preferred mode of this stretchable sanitary napkin 10, the central portion of the layer of capillary channel fibers 88 can be gathered into a small "loop" or "tuft" 92. This loop or tuft 92 thus extends upward from the layer of capillary channel fibers to firmly contact the topsheet 25. Moreover, the loop or tuft 92 is positioned centrally in the overall article, such that it can provide rapid acquisition and transport of fluid into the remaining portion of the layer of capillary channel fibers, and thence into the fluid storage layer of the article.

Advantageously, such "loop" or "tuft" not only concentrates capillary channel fibers at the point where fluid impinges onto the article, but also orients the capillary channel fibers which comprise the loop or tuft substantially in the upward z-direction, thus enhancing fluid movement in the downward z-direction of the article. The following Example illustrates an absorbent article having a substantially central, z-directional tuft of capillary channel fibers.

EXAMPLE II

A layer of capillary channel fibers of the type disclosed herein (with a 6-inch length) is gathered in its center to provide a slightly raised oval "tuft" having the approximate dimensions: 2–3 inches x-direction (or longitudinal dimension); 1.5 inches y-direction (or lateral dimension) at widest point; and 5 mm–10 mm z-direction.

The tufted bundle of fibers can be held in its tufted configuration by any convenient means. Typically, the tuft is passed through a confining slit in a sheet of paper or hydrophilic polymer. Using the procedures disclosed herein, the tufted bundle of fibers is assembled into an absorbent article with the tuft residing approximately at the center of the overlying topsheet, and with the tuft in close contact with the topsheet, as explained hereinabove.

In use as a sanitary napkin, the article is positioned (e.g., intralabially) to maximize fluid uptake by the tuft. In an alternate mode, the ends of the looped fibers in the tuft are cut to provide a fleece-like, z-directional bundle of open-ended capillary channel fibers. In still another embodiment, the layer of capillary channel fibers comprising the base of the tuft is positioned wholly or partly within the wet-laid or dry-laid absorbent core of the article, rather than atop the core. In this latter embodiment, a commercially-available layered laminate core comprising two outer tissue layers with an intermediate layer of absorbent gelling material (AGM) can be used. The capillary channels at the base of the tuft can be slipped into the internal, AGM-containing layer.

While particular embodiments of the present invention have been illustrated and described, it would be obvious to those skilled in the art that various other changes and modifications can be made without departing from the spirit and scope of the invention.

What is claimed is:

1. A sanitary napkin having a length, a width, a longitudinal centerline, a stiffened longitudinal central region disposed along the length of at least a portion of the longitudinal centerline, and longitudinal side regions outboard of the longitudinal central region, a flexure resistance as measured through said longitudinal side regions and a flexure resistance as measured through said stiffened longitudinal central region, said sanitary napkin comprising:

a liquid pervious topsheet;

a liquid impervious backsheet joined to said topsheet;

an absorbent core positioned between said topsheet and said backsheet;

wherein said stiffened longitudinal central region has a length that is less than one half the length of said sanitary napkin, said longitudinal side regions have absorbent capacity, and the flexure resistance of said sanitary napkin as measured through said longitudinal central region is greater than the flexure resistance of said sanitary napkin as measured through the longitudinal side regions, and said sanitary napkin has a caliper as measured through said longitudinal side regions of less than about 5 mm.

2. The sanitary napkin of claim 1 having a caliper as measured through said longitudinal side regions of less than or equal to about 3 mm.

3. The sanitary napkin of claim 2 wherein the width of said longitudinal central region is less than or equal to about 5 cm.

4. The sanitary napkin of claim 3 wherein the flexure resistance of said sanitary napkin as measured through said longitudinal central region is at least about 25% greater than the flexure resistance of said sanitary napkin as measured through said longitudinal side regions.

5. The sanitary napkin of claim 3 wherein the flexure resistance of said sanitary napkin as measured through said longitudinal central region is at least about 50% greater than the flexure resistance of said sanitary napkin as measured through said longitudinal side regions.

6. The sanitary napkin of claim 4 wherein the flexure resistance of said sanitary napkin measured through said longitudinal central region is less than or equal to about 700 grams force.

7. The sanitary napkin of claim 4 wherein the flexure resistance of said sanitary napkin measured through said longitudinal side regions is less than or equal to about 600 grams force.

8. The sanitary napkin of claim 4 wherein the stiffened longitudinal central region is comprised of components comprising at least: said topsheet, backsheet, and absorbent core; and said stiffened longitudinal central region is stiffer than the surrounding longitudinal side regions by being provided with a structure selected from the group consisting of: (1) a longitudinal central region with an increased caliper; (2) at least one of the components comprising the longitudinal central region being folded to create double, or more, thickness of the said at least one of said components; (3) at least one of the components of the longitudinal central region comprising several layers; (4) at least one of the components of the longitudinal central region comprising stiffer materials; (5) at least one of the components of the longitudinal central region having a higher basis weight in the longitudinal central region; or (6) one or more additional components in the longitudinal central region.

9. The sanitary napkin of claim 4 additionally comprising a stiffening material positioned between said topsheet and said backsheet and centered along said longitudinal centerline in said longitudinal central region.

10. The sanitary napkin of claim 4 additionally comprising a stiffening material positioned between said topsheet and said backsheet and centered along said longitudinal centerline in said longitudinal central region.

11. The sanitary napkin of claim 4 additionally comprising a stiffening material positioned on said backsheet and centered along said longitudinal centerline in said longitudinal central region.

12. The sanitary napkin of claim 4 wherein a 66.5 cm$^2$ sample cut from a portion of the sanitary napkin that would be centered under the vaginal orifice when the sanitary napkin is worn has a test capacity for absorbing sterile saline of at least about 8.0 grams of sterile saline when submerged in sterile saline for 10 minutes and said entire sanitary napkin has a total capacity of at least about 22.0 grams under the same conditions.

13. A sanitary napkin having a longitudinal centerline, a stiffened longtudinal central region disposed along the length of at least a portion of the longitudinal centerline, a transverse centerline, two longitudinal edges, two end edges, a first end region extending from one of said end edges toward said transverse centerline, a second end region extending from the other end edge toward said transverse centerline, and a central region between said first and second end regions, a flexure resistance as measured through said end regions and a flexure resistance as measured through said stiffened longitudinal central region, said sanitary napkin comprising:

a liquid pervious topsheet;

a liquid impervious backsheet joined to said topsheet;

an absorbent core positioned between said topsheet and said backsheet, said absorbent core having two longitudinal edges and a width defined by said longitudinal edges;

wherein said stiffened longitudinal central region has a transverse width greater than or equal to about 5 cm, said longitudinal side regions have absorbent capacity, and the flexure resistance of said sanitary napkin as measured through said central region is greater than the flexure resistance of said sanitary napkin as measured through said first and second end regions, and said sanitary napkin has a caliper as measured through said first and second end regions of less than about 5 mm.

14. The sanitary napkin of claim 13 having a caliper as measured through said first and second end regions of less than or equal to about 3 mm.

15. The sanitary napkin of claim 14 wherein said first and second end regions extend from the end edges of the sanitary napkin between about ⅛ and ⅓ of the length of said sanitary napkin toward the transverse centerline.

16. The sanitary napkin of claim 15 wherein the flexure resistance of said sanitary napkin as measured through said central region is at least about 25% greater than the flexure resistance of said sanitary napkin as measured through said first and second end regions.

17. The sanitary napkin of claim 15 wherein the flexure resistance of said sanitary napkin as measured through said central region is at least about 50% greater than the flexure resistance of said sanitary napkin as measured through said first and second end regions.

18. The sanitary napkin of claim 16 wherein the flexure resistance of said sanitary napkin as measured through said central region is less than or equal to about 700 grams force.

19. The sanitary napkin of claim 16 wherein the flexure resistance of said sanitary napkin as measured through said first and second end regions is less than or equal to about 600 grams force.

* * * * *